United States Patent [19]

Diehr et al.

[11] Patent Number: 4,820,337
[45] Date of Patent: Apr. 11, 1989

[54] 1-(2-OXYAMINOSULPHONYLPHENYLSULPHONYL)-3-TRIAZINYL-UREAS

[75] Inventors: Hans-Joachim Diehr; Christa Fest, both of Wuppertal; Rolf Kirsten, Monheim; Joachim Kluth, Langenfeld; Klaus-Helmut Müller, Duesseldorf; Theodor Pfister, Monheim; Uwe Priesnitz, Solingen; Hans-Jochem Riebel, Wuppertal; Wolfgang Roy, Langenfeld; Hans-Joachim Santel, Cologne; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 30,195

[22] Filed: Mar. 24, 1987

Related U.S. Application Data

[63] Continuation-in-part of Ser. No. 769,224, Aug. 23, 1985, Pat. No. 4,666,505, and Ser. No. 889,978, Jul. 24, 1986.

[30] Foreign Application Priority Data

Aug. 30, 1984 [DE] Fed. Rep. of Germany ....... 3431929
May 25, 1985 [DE] Fed. Rep. of Germany ....... 3518876
Aug. 6, 1985 [DE] Fed. Rep. of Germany ....... 3528100

[51] Int. Cl.$^4$ ................. C07D 251/42; C07D 251/48; C07D 251/18; A01N 43/66
[52] U.S. Cl. ........................................ 71/93; 544/206; 544/208; 544/211; 71/92
[58] Field of Search ................... 71/93; 544/211, 206, 544/208

[56] References Cited

U.S. PATENT DOCUMENTS

| 4,310,346 | 1/1982 | Levitt et al. | 544/208 |
| 4,372,778 | 2/1983 | Levitt | 71/94 |
| 4,417,917 | 11/1983 | Levitt et al. | 544/211 |
| 4,604,131 | 8/1986 | Hanagan | 544/206 |
| 4,609,398 | 9/1986 | Nicholson et al. | 544/211 |
| 4,626,273 | 12/1986 | Shiokawa et al. | 71/92 |
| 4,658,027 | 4/1987 | Diehr et al. | 544/182 |

FOREIGN PATENT DOCUMENTS

| 0048143 | 3/1982 | |
| 0074282 | 3/1983 | European Pat. Off. |
| 0085028 | 8/1983 | European Pat. Off. |
| 0102925 | 3/1984 | European Pat. Off. |
| 0116518 | 8/1984 | European Pat. Off. |
| 0128274 | 12/1984 | European Pat. Off. |

Primary Examiner—John M. Ford
Attorney, Agent, or Firm—Sprung Horn Kramer & Woods

[57] ABSTRACT

Herbicidally active 1-(2-oxyaminosulphenylphenylsulphonyl)-3-triazinyl-ureas of the formula

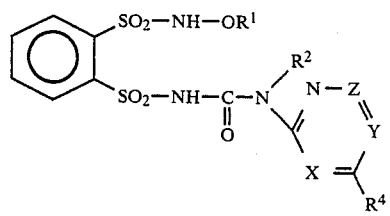

in which
X is nitrogen,
Y is nitrogn,
Z is C-R$^6$ and
R$^1$, R$^2$, R$^4$ and R$^6$ are various organic radicals.

4 Claims, No Drawings

1-(2-OXYAMINOSULPHONYLPHENYLSULPHONYL)-3-TRIAZINYL-UREAS

This is a continuation-in-part of application Ser. No. 769,224, filed Aug. 23, 1985, now U.S. Pat. No. 4,666,505, and application Ser. No. 889,978, filed July 24, 1986, now pending.

The invention relates to new 1-(2-oxyaminosulphonylphenylsulphonyl)-3-heteroaryl-ureas, processes for their preparation and their use as herbicides.

It is known that certain 1-arylsulphonyl-3-heteroaryl-ureas, such as, for example, 1-(2-methoxyphenylsulphonyl)-3-(4,6-dimethyl-pyrimidin-2-yl)-urea, have a herbicidal action. However, the action of these compounds is not always completely satisfactory (compare U.S. Pat. No. 4,169,719).

New 1-(2-oxyaminosulfphonylphenylsulphonyl)-3-heteroaryl-ureas of the general formula (I)

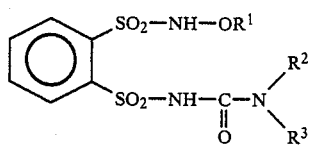

in which
R$^1$ represents an optionally substituted radical from the series comprising alkyl, alkenyl, alkinyl, cycloalkyl, cycloalkylalkyl, aralkyl and aryl,
R$^2$ represents hydrogen or an optionally substituted radical from the series comprising alkyl, alkenyl, alkinyl and aralkyl and
R$^3$ represents an optionally substituted and/or optionally fused six-membered aromatic heterocyclic radical containing at least one nitrogen atom, have now been found, the following compounds being excluded: 1-(2-methoxyaminosulphonylphenylsulphonyl)-, 1-(2-ethoxyaminosulphonylphenylsulphonyl)-, 1-(2-propoxyaminosulphonylphenylsulphonyl)-, 1-(2-isopropoxyaminosulphonyl)- and 1-(2-butoxyaminosulphonylphenylsulphonyl), -3-(4,6-dimethyl-pyrimidin-2-yl)-urea, -3-(4,6-diethyl-pyrimidin-2-yl)-urea, -3-(4,6-dipropylpyrimidin-2-yl)-urea, -3-(4,6-diisopropyl-pyrimidin-2-yl)-urea and -3-(4,6-dibutyl-pyrimidin-2-yl)-urea.

The new compounds of the formula (I) are obtained by a process in which (a) benzodisultams of the formula (II)

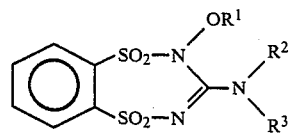

in which
R$^1$, R$^2$ and R$^3$ have the abovementioned meanings, are reacted with water, if appropriate in the presence of bases and if appropriate in the presence of diluents, or (b) benzene-1,2-disulphonic acid dichloride of the formula (III)

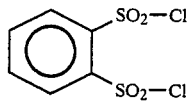

is reacted with oxyguanidine derivatives of the formula (IV)

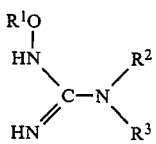

in which
R$^1$, R$^2$ and R$^3$ have the abovementioned meaning, in the presence of acid acceptors and if appropriate in the presence of diluents, and the compounds of the formula (II) thereby obtained are reacted—without intermediate isolation—with water, if appropriate in the presence of bases and if appropriate in the presence of diluents.

The new 1-(2-oxyaminosulphonylphenylsulphonyl)-3-heteroaryl-ureas of the formula (I) are distinguished by a powerful herbicidal activity.

Surprisingly, the new compounds of the formula (I) exhibit a considerably better herbicidal action than the already known urea drivatives of the same type of action.

The invention preferably relates to compounds of the formula (I) in which
R$^1$ represents C$_1$-C$_{12}$-alkyl [which is optionally substituted by fluorine, chlorine, cyano, C$_1$-C$_4$-alkoxy, C$_1$-C$_4$-alkylthio, C$_1$-C$_4$-alkylsulphinyl, C$_1$-C$_4$-alkylsulphonyl, C$_1$-C$_4$-alkyl-carbonyl, C$_1$-C$_4$-alkoxy-carbonyl, C$_1$-C$_4$-alkylamino-carbonyl or di-(C$_1$-C$_4$-alkyl)-amino-carbonyl], or represents C$_3$-C$_6$-alkenyl [which is optionally substituted by fluorine, chlorine or bromine], C$_3$-C$_6$-alkinyl, C$_3$-C$_6$-cycloalkyl, C$_3$-C$_6$-cycloalkyl-C$_1$-C$_2$-alkyl or phenyl-C$_1$-C$_2$-alkyl [which is optionally substituted by fluorine, chlorine, nitro, cyano, C$_1$-C$_4$-alkyl, C$_1$-C$_4$-alkoxy or C$_1$-C$_4$-alkoxy-carbonyl], or represents benzhydryl, or represents phenyl [which is optionally substituted by fluorine, chlorine, nitro, cyano, C$_1$-C$_4$-alkyl, trifluoromethyl, C$_1$-C$_4$-alkoxy, C$_1$-C$_2$-fluoroalkoxy, C$_1$-C$_4$-alkylthio, trifluoromethylthio or C$_1$-C$_4$-alkoxy-carbonyl],
and in which, furthermore,
R$^2$ represents hydrogen or C$_1$-C$_4$-alkyl [which is optionally substituted by fluorine, chlorine, cyano, C$_1$-C$_4$-alkoxy, C$_1$-C$_4$-alkylthio, C$_1$-C$_4$-alkylsulphinyl, C$_1$-C$_4$-alkylsulphonyl, C$_1$-C$_4$-alkyl-carbonyl, C$_1$-C$_4$-alkoxy-carbonyl, C$_1$-C$_4$-alkylamino-carbonyl or di-(C$_1$-C$_4$-alkyl)-amino-carbonyl], or represents C$_3$-C$_6$-alkenyl, C$_3$-C$_6$-alkinyl or phenyl-C$_1$-C$_2$-alkyl [which is optionally substituted by fluorine, chlorine, nitro, cyano, C$_1$-C$_4$-alkyl, C$_1$-C$_4$-alkoxy or C$_1$-C$_4$-alkoxy-carbonyl],
and in which, furthermore,
R$^3$ represents the radical

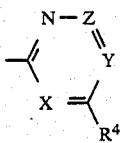

wherein

R[4] represents hydrogen, fluorine, chlorine, bromine, hydroxyl, $C_1$-$C_4$-alkyl [which is optionally substituted by fluorine and/or chlorine], $C_1$-$C_4$-alkoxy [which is optionally substituted by fluorine and/or chlorine], $C_1$-$C_4$-alkylthio [which is optionally substituted by fluorine and/or chlorine], amino, $C_1$-$C_4$-alkylamino or di($C_1$-$C_4$-alkyl)-amino, X represents nitrogen, Y represents nitrogen, Z represents an optionally substituted methine bridge C-R[6], wherein R[6] represents hydrogen, fluorine, chlorine, bromine, hydroxyl, $C_1$-$C_4$-alkyl [which is optionally substituted by fluorine and/or chlorine], $C_1$-$C_4$-alkoxy [which is optionally substituted by fluorine and/or chlorine], $C_1$-$C_4$-alkylthio [which is optionally substituted by fluorine and/or chlorine], amino, $C_1$-$C_4$-alkylamino or di-($C_1$-$C_4$-alkyl)-amino, the compounds mentioned above by name being excluded.

The invention particularly relates to compounds of the formula (I) in which

R[1] represents $C_1$-$C_8$-alkyl [which is optionally substituted by fluorine or chlorine], $C_3$-$C_4$-alkenyl, $C_1$-$C_2$-alkoxy-carbonylmethyl, phenyl, phenethyl or benzyl [which is optionally substituted by fluorine, chlorine, nitro, cyano, methyl, methoxy or methoxy-carbonyl], R[2] represents hydrogen and R[3] represents the radical

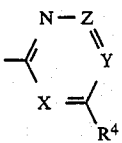

wherein

R[4] represents chlorine, methyl, ethyl, methoxy, difluoromethoxy or ethoxy,

X represents nitrogen,

Y represents nitrogen, and

Z represents an optionally substituted methine bridge C—R[6], wherein

R[6] represents hydrogen, chlorine, methyl, methoxy, ethoxy, methylthio, ethylthio, methylamino or ethylamino, the compounds mentioned above by name being excluded.

The chemical reaction which takes place in the preparation process according to the invention described above under (a) can be outlined, for example, by the following equation:

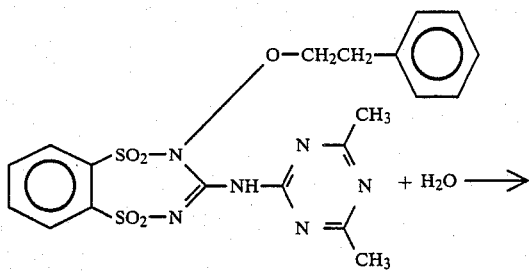

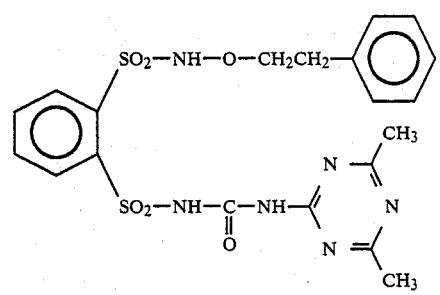

The reactions which take place in the preparation process according to the invention described above under (b) can be outlined, for example, by the following equation:

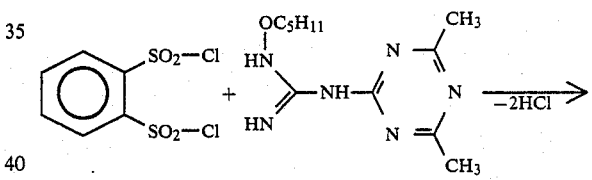

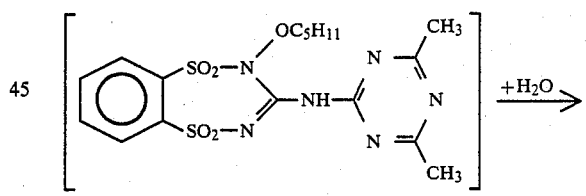

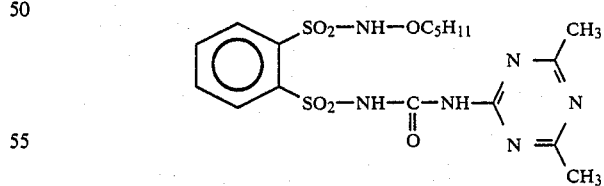

Formula (II) provides a general definition of the benzodisultams to be used as starting substances in process (a) according to the invention.

In formula (II), R[1], R[2] and R[3] preferably and particularly have the same meanings as are given above as preferred or as particularly preferred in the context of the definition of the substituents for formula (I).

Examples of starting substances of formula (II) are listed in the following Table 1.

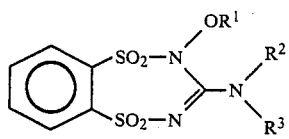
(II)
TABLE 1
| Examples of starting substances of the formula (II) | | |
|---|---|---|
| R¹ | R² | R³ |
| -CH₂-C₆H₄-F (2-fluorobenzyl) | H | pyrimidine with CH₃, CH₃ |
| -CH₃ | CH₃ | pyrimidine with CH₃, OCH₃ |
| -CH₂-C₆H₄-Cl (2-chlorobenzyl) | H | pyrimidine with CH₃, CH₃ |
| -C₃H₇ | H | pyrimidine with CH₃, OCH₃ |
| -CH(CH₃)₂ | H | pyrimidine with CH₃, OCH₃ |
| -C₄H₉ | H | pyrimidine with CH₃, OCH₃ |
| -CH₂CH(CH₃)₂ | H | pyrimidine with CH₃, OCH₃ |

TABLE 1-continued

| Examples of starting substances of the formula (II) | | |
|---|---|---|
| R¹ | R² | R³ |
| $-C_8H_{17}$ | H | pyrimidine with 4-CH₃, 6-CH₃ |
| $-CH_2-C_6H_5$ | H | pyrimidine with 4-CH₃, 6-CH₃ |
| $-CH_2CH_2-C_6H_5$ | H | pyrimidine with 4-CH₃, 6-CH₃ |
| $-CH_2-C_6H_4-CH_3$ (para) | H | pyrimidine with 4-CH₃, 6-CH₃ |
| $-CH_2CH=CH_2$ | H | pyrimidine with 4-CH₃, 6-CH₃ |
| $-CH_3$ | H | pyrimidine with 4-CH₃, 6-OCH₃ |
| $-C_2H_5$ | H | pyrimidine with 6-CH₃ |
| $-CH_2CH=CH_2$ | H | pyrimidine with 4-OCH₃, 6-OCH₃ |
| $-CH_2CH(CH_3)_2$ | H | pyrimidine with 4-Cl, 6-CH₃ |

TABLE 1-continued

Examples of starting substances of the formula (II)

| R¹ | R² | R³ |
|---|---|---|
| —CH₃ | H | pyrimidine with CH₃ and OC₂H₅ substituents |
| —C₂H₅ | H | pyrimidine with Cl and OCH₃ substituents |
| —CH₃ | H | pyrimidine with Cl and OC₂H₅ substituents |
| —CH₂—C₆H₅ | H | pyrimidine with Cl and N(CH₃)₂ substituents |
| —CH₃ | H | pyrimidine with CH₃ and SCH₃ substituents |
| —C₂H₅ | H | pyrimidine with CH₃ and N(CH₃)₂ substituents |
| —CH₃ | H | pyrimidine with OCH₃ and OCH₃ substituents |
| —CH₂CH=CH₂ | H | pyrimidine with CH₃ and OCHF₂ substituents |

TABLE 1-continued

| R¹ | R² | R³ |
|---|---|---|
| —CH₃ | H | 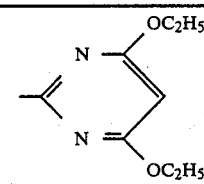 |
| —CH₃ | —C₂H₅ | 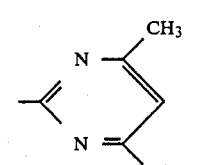 |
| —C₃H₇(—n) | H | 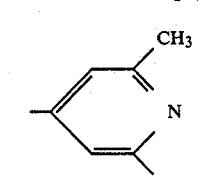 |
| —CH₂COOC₂H₅ | H | 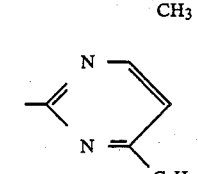 |
| —CH₃ | H | 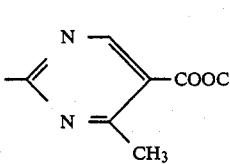 |

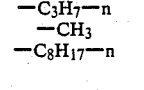 (IIa)

TABLE 1a
Examples of starting substances of the formula (IIa)

| R¹ | R⁸ | R⁹ |
|---|---|---|
| —CH₃ | —OCH₃ | —OCH₃ |
| —C₂H₅ | —OCH₃ | —OCH₃ |
| —CH₂—CH=CH₂ | —OCH₃ | —OCH₃ |
| —CH₃ | —OCH₃ | —OCH₃ |
| —C₄H₉—n | —OCH₃ | —OC₂H₅ |
| —CH₃ | —OCH₃ | —OC₂H₅ |
| —C₃H₇—n | —OCH₃ | —N(C₂H₅)₂ |
| —CH₃ | —SCH₃ | —NH—C₂H₅ |
| —C₈H₁₇—n | —CH₃ | —OCH₃ |
| —CH₂—⌬ 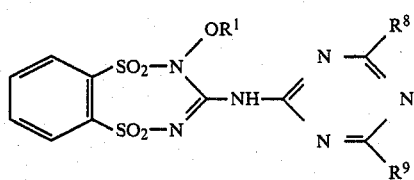 | —CH₃ | —OCH₃ |
| —CH₃ | —OCH₃ | —SCH₃ |
| —CH₃ | —CH₃ | —OC₂H₅ |

TABLE 1a-continued
Examples of starting substances of the formula (IIa)

| R¹ | R⁸ | R⁹ |
|---|---|---|
| —CH₂—⌬ | —CH₃ | —OC₂H₅ |
| —CH₃ | —SCH₃ | —NHC₂H₅ |
| —CH₃ | —C₂H₅ | —OCH₃ |
| —CH₃ | —CH₃ | —CH₃ |
| —CH₂—CH=CH₂ | —CH₃ | —CH₃ |

The compounds of the formula (II) have not yet been described in the literature. The compounds of the formula (II) are obtained by a process in which benzene-1,2-disulphonic acid dichloride of the formula (III)

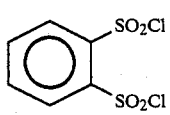 (III)

is reacted with oxyguanidine derivatives of the formula (IV)

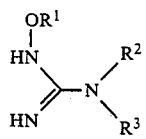

in which

R¹, R² and R³ have the abovementioned meaning, in the presence of acid acceptors, such as, for example, pyridine or diazabicyclooctane (DABCO), and, if appropriate, in the presence of diluents, such as, for example, methylene chloride, chloroform, tetrahydrofuran or dioxane, at temperatures between −30° C. and +50° C.

Working up can be effected by customary methods, for example by concentrating the mixture, taking up the residue in methylene chloride, washing the mixture with dilute hydrochloric acid and with water and separating off, drying, filtering and concentrating the organic phase, the products of the formula (II) remaining in the residue.

The benzene-1,2-disulfphonic acid dichloride of the formula (III) to be used as the starting substance is already known (compare J. Org. Chem. 31, (1966), 3289–3292).

Formula (IV) provides a general definition of the oxyguanidine derivatives also to be used as starting substances. In formula (IV), R¹, R² and R³ preferably and particularly have the same meanings as are given above as preferred or as particularly preferred in the context of the definition of the substituents for formula (I).

Examples which may be mentioned for starting substances of the formula (IV) are: N'-(4-methyl-pyrimidin-2-yl)-, N'-(4-ethyl-pyrimidin-2-yl)-, N'-(4,6-dimethoxypyrimidin-2-yl)-, N'-(2,6-dimethyl-pyrimidin-4-yl)-, N'-(4-difluoromethoxy-6-methyl-pyrimidin-2-yl), N'-(2,6-dimethyl-pyrimidin-4-yl)-, N'-(4,6-dimethyl-pyrimidin-2-yl)-, N'-(4-methoxy-6-methyl-pyrimidin-2-yl)-, N'-(4-ethoxy-6-methyl-pyrimidin-2-yl)-, N'-(4-chloro-6-methoxy-pyrimidin-2-yl)-, N'-(4-chloro-6-ethoxy-pyrimidin-2-yl)-, N'-(4-chloro-6-dimethylamino-pyrimidin-2-yl)-, N'-(4-methyl-6-methylthiopyrimidin-2-yl)-, N'-(4-dimethylamino-6-methylpyrimidin-2-yl)-N'-(4,6-dimethyl-s-triazin-2-yl)-, N'-(4-methoxy-6-methyl-s-triazin-2-yl)-, N'-(4-ethoxy-6-methyl-s-triazin-2-yl)-, N'-(4,6-dimethoxy-s-triazin-2-yl)-, N'-(4,6-diethoxy-s-triazin-2-yl)-, N'-(4-ethoxy-6-methoxy-s-triazin-2-yl)-, N'-(4-methyl-6-methylthio-s-triazin-2-yl)-, N'-(4-ethylthio-6-methyl-s-triazin-2-yl)-, N'(4-methoxy-6-methylthio-s-triazin-2-yl)-, N'-(4-ethoxy-6-methylthio-s-triazin-2-yl)-, N'-(4-ethylthio-6-methoxy-s-triazin-2-yl)-, N'-(4-ethoxy-6-ethylthio-s-triazin-2-yl)-, N'-(4,6-bis-methylthio-s-triazin-2-yl)-, N'-4,6-(bis-ethylthio-s-triazin-2-yl)-, N'-(4-methyl-6-methylamino-s-triazin-2-yl)-, N'-(4-ethylamino-6-methyl-s-triazin-2-yl)-, N'-(4-dimethylamino-6-methyl-s-triazin-2-yl)-, N'-(4-diethylamino-6-methyl-s-triazin-2-yl)-, N'-(4-methoxy-6-methylamino-s-triazin-2-yl)-, N'-(4-ethylamino-6-methoxy-s-triazin-2-yl)-, N'-(4-dimethylamino-6-methoxy-s-triazin-2-yl)-, N'-(4-diethylamino-6-methoxy-s-triazin-2-yl)-, N'-(4-ethoxy-6-methylamino-s-triazin-2-yl)-, N'-(4-ethoxy-6-ethylamino-s-triazin-2-yl)-, N'-(4-dimethylamino-6-ethoxy-s-triazin-2-yl)-, N'-(4-diethylamino-6-ethoxy-s-triazin-2-yl)-, N'-(4-methylamino-6-methylthio-s-triazin-2-yl)-, N'-(4-ethylamino-6-methyl-thio-s-triazin-2-yl)-, N'-(4-dimethylamino-6-methylthio-s-triazin-2-yl)-, N'-(4-diethylamino-6-methylthio-s-triazin-2-yl)-, N'-(4-ethylthio-6-methylamino-s-triazin-2-yl)-, N-(4-dimethylamino-6-ethylthio-s-triazin-2-yl)- and N'-(4-diethylamino-6-ethylthio-s-triazin-2-yl)-N''-methoxyguanidine, -N''-ethoxy-guanidine, -N''-propoxy-guanidine, -N''-isopropoxyguanidine, -N''-butoxy-guanidine, -N''-isobutoxy-guanidine, -N''-sec.-butoxy-guanidine, -N''-pentoxy-guanidine, -N''-isopentoxy-guanidine, -N''-hexyloxy-guanidine, -N''-octyloxyguanidine, -N''-allyloxyguanidine, -N''-(2-chloroethoxy)-guanidine, -N''-(2-fluoro-ethoxy)-guanidine, -N''-(2-chloro-propoxy)-guanidine, -N''-(2-fluoro-propoxy)-guanidine, -N''-(3-chloro-propoxy)-guanidine, -N''-(4-chloro-butoxy)-guanidine, -N''-methoxycarbonylmethoxyguanidine, -N''-ethoxycarbonylmethoxy-guanidine, -N''-(1-methoxycarbonyl-ethoxy)-guanidine, -N''-(1-ethoxycarbonylethoxy)-guanidine, -N''-dimethylaminocarbonylmethoxyguanidine, -N''-(2-phenyl-ethoxy)-guanidine, -N''-phenoxy-guanidine, -N''-(4-methyl-benzyloxy)-guanidine, -N''-(4-fluoro-benzyloxy)-guanidine, -N''-(4-chloro-benzyloxy)-guanidine, -N''-(4-nitrobenzyloxy)-guanidine, -N''-(2,6-dichloro-benzyloxy)-guanidine, -N''-(4-methoxycarbonylbenzyloxy)-guanidine and -N''-(4-ethoxycarbonyl-benzyloxy)-guanidine.

The starting substances of the formula (IV) are known in some cases (compare J. Chem. Soc. 1962, page 3915 and DE-OS (German Published Specification) No. 3,334,455).

The compounds of the formula (IV) are obtained by a process in which cyanamide derivatives of the formula (V)

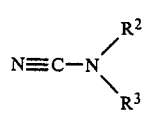

in which

R² and R³ have the abovementioned meanings, are reacted with hydroxylamine derivatives of the formula (VI)

$$H_2N{-}OR^1 \qquad (VI)$$

in which

R¹ has the abovementioned meanings, or with hydrochlorides of hydroxylamine derivatives of the formula (VI), if appropriate in the presence of diluents, such as, for example, ethanol, propanol or butanol, at temperatures between 20° C. and 120° C. and, if appropriate, the reaction products are treated with acid acceptors, such as, for example, ammmonia, potassium carbonate or sodium hydroxide.

The cyanamide derivatives of the formula (V) are known in some cases (compare J. Chem. Soc. 1953, 1725). The compounds of the formula (V) are essentially obtained by the following synthesis routes:

(a) by reaction of alkali metal or alkaline earth metal salts of cyanamide—such as, for example, sodium cyanamide or calcium cyanamide—with chloro-hetarenes of the formula (VII)

$R^3$ has the abovementioned meaning, and, if appropriate, subsequently—if $R^2$ does not represent hydrogen—with halogen compounds of the formula (VIII)

$$Q-R^2 \qquad \text{(VIII)}$$

in which $R^2$ represents an optionally substituted radical from the series comprising alkyl, alkenyl, alkinyl and aralkyl and Q represents chlorine, bromine or iodine, if appropriate in the presence of inert diluents, such as, for example, acetone, acetonitrile or dimethylformamide, at temperatures between 0° C. and 100° C.

After the mixture has been concentrated and the residue has been dissolved in water, the cyanamide derivatives of the formula (V) can be precipitated by acidification, for example with hydrochloric acid, and isolated by filtration with suction.

Alternatively, the compounds of the formula (V) are obtained (b) in the case where $R^3$ represents a substituted pyrimidinyl radical, by reaction of cyanoguanidine ("dicyandiamide") with β-dicarbonyl compounds or derivatives thereof, such as acetylacetone (compare J. Chem. Soc. 1953, 1725–1730); acetoacetic acid esters (compare J. Prakt. Chem. 77 (1908), 542 and J. Chem. Soc. 1948, 586) or malonic acid esters (compare German Patent Specification 158,591).

The 2-cyanoamino-4-hydroxy-6-methyl- or -4,6-dihydroxy-pyrimidines obtained from acetoacetic acid esters or malonic acid esters can be converted into corresponding 2-cyanoamino-4-alkoxy-6-methyl- or -4,6-dialkoxy-pyrimidines in a known manner by reaction with alkylating agents, such as, for example, dimethyl sulphate or diethyl sulphate, if appropriate in the presence of diluents, such as, for example, water, methanol, ethanol, n- or iso-propanol, acetone, dioxane or dimethylformamide, and in the presence of acid-binding agents, such as, for example, sodium hydroxide or potassium hydroxide or sodium carbonate or potassium carbonate. To avoid N-alkylation, acylation is carried out, if appropriate, with an acylating agent, such as, for example, acetic anhydride or acetyl chloride, and, after the alkylation, the product is deacylated again with aqueous acids or bases.

In another alternative process, the compounds of the formula (V) are obtained by a process in which (c) amino-hetarenes of the formula (IX)

$$H_2N-R^3 \qquad \text{(IX)}$$

in which $R^3$ has the abovementioned meaning, are reacted with carbonyl isothiocyanates of the formula (X)

in which $R^7$ represents ethoxy or phenyl, if appropriate in the presence of an inert diluent, such as, for example, acetone, acetonitrile or toluene, at temperatures between 0° C. and 100° C., the carbonylthioureas of the formula (XI) thereby formed

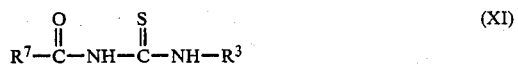

in which $R^3$ and $R^7$ have the abovementioned meanings, are isolated by filtration with suction, if appropriate after concentration of the mixture, and are reacted with aqueous alkali metal or alkaline earth metal hydroxide solutions, such as, for example, sodium hydroxide solution, if appropriate in the presence of an organic solvent, such as, for example, tetrahydrofuran or dioxane, at temperatures between 0° C. and 120° C., and the thioureas obtained as crystals after acidification, for example with hydrochloric acid, of the formula (XII)

in which $R^3$ has the abovementioned meaning, are isolated by filtration with suction and reacted with metal compounds which can bond hydrogen sulphide, such as, for example, lead-II acetate, copper-II acetate, mercury-II acetate or iron-II acetate, in the presence of aqueous alkali metal or alkaline earth metal hydroxide solutions, such as, for example, sodium hydroxide solution, at temperatures between 20° C. and 100° C., and, when the reaction has ended, the mixture is filtered and the filtrate is acidified with an acid, such as, for example, acetic acid. The products of the formula (V) thereby obtained as crystals can be isolated by filtration with suction.

The starting substances for the preparation processes described above under (a), (b) and (c) for the cyanamide derivatives of the formula (V) are known and/or can be prepared by processes which are known per se.

These include the chloro-hetarenes of the formula (VII) (compare J. Chem. Soc. (c) 1966, 2031; Chem. Pharm. Bull. 11 (1963), 1382–1388 and Arch. Pharm. 295, (1962), 649–657), the halogen compounds of the formula (VIII) (commercially available chemicals), the amino-hetarenes of the formula (IX) (compare Chem. Pharm. Bull. 11, (1963) pages 1382–1388; J. Chem. Soc. 1946, 81 and U.S. Pat. No. 4,299,960) and the carbonyl isothiocyanates of the formula (X) (compare J. Heterocycl. Chem. 5, (1968), 837 and U.S. Pat. No. 4,160,037).

The benzene-1,2-disulphonic acid dichloride of the formula (III) to be used as the starting substance in process (b) according to the invention is already known (compare J. Org. Chem. 31, (1966), 3289–3292).

Formula (IV) provides a general definition of the oxyguanidine derivatives to be used as starting substances in process (b) according to the invention. In formula (IV), $R^1$, $R^2$ and $R^3$ preferably and particularly have the same meanings as are given above as preferred or as particularly preferred in the context of the definition of the substituents of formula (I).

Examples of compounds of the formula (IV) have already been mentioned above in connection with the description of the starting substances for process (a). The preparation of the starting substances of the formula (IV) has already been described above in connection with the description of the starting substances for process (a).

Process (a) according to the invention for the preparation of the new compounds of the formula (I) is preferably carried out in water as the solvent. Other possible diluents are all the inert organic solvents, but preferably aprotic polar solvents. These include, where appropriate, ketones, such as, for example, acetone and methyl ethyl ketone, nitriles, such as, for example, acetonitrile and propionitrile, dimethylsulphoxide, sulpholane, 1,2-dimethoxyethane and dioxane.

Process (a) is carried out in the presence of bases. Preferred possible bases are alkali metal or alkaline earth metal hydroxides, such as, for example, sodium hydroxide, potassium hydroxide and calcium hydroxide, tertiary amines, such as, for example, triethylamine, N,N-dimethylaniline and N,N-dimethyl-benzylamine, and nitrogen-containing heterocyclic compounds, such as, for example, pyridine or diazabicyclooctane (DABCO).

The reaction temperatures can be varied within a substantial range in process (a) according to the invention. In general, the reaction is carried out between 0° C. and +100° C., preferably between 10° C. and +80° C. Process (a) according to the invention is in general carried out under normal pressure.

For carrying out process (a), in general between 1 and 100 moles, preferably between 5 and 50 moles, of water and, if appropriate, between 1 and 3 moles, preferably between 1 and 2 moles, of a base are employed per mole of benzodisultam of the formula (II).

The reaction components are usually brought together at room temperature and the reaction mixture is stirred until the reaction has ended.

Working up can be carried out in the customary manner; for example, by a procedure in which the mixture is acidified—for example with hydrochloric acid—and concentrated to approximately half the volume, and the product of the formula (I) obtained as crystals is isolated by filtration with suction.

Process (b) according to the invention for the preparation of the new compounds of the formula (I) is preferably carried out using diluents. Possible diluents are virtually all the inert organic solvents, preferably aprotic polar solvents. These include optionally substituted hydrocarbons, such as, for example, methylene chloride, chloroform, 1,2-dichloroethane, toluene, xylene and chlorobenzene, nitriles, such as, for example, acetonitrile and propionitrile, ethers, such as, for example, 1,2-dimethoxyethane, tetrahydrofuran and dioxane, and dimethylformamide, dimethylacetamide, dimethylsulphoxide, sulpholane, pyridine and 2-methyl-5-ethylpyridine.

Virtually all the acid-binding agents which are usually employed can be used as acid acceptors in process (b). These include, in particular, alkali metal and alkaline earth metal hydroxides, alkali metal and alkaline earth metal hydrides, organometallic compounds, such as butyl-lithium, and furthermore aliphatic, aromatic or heterocyclic amines, such as trimethylamine, triethylamine, N,N-dimethylaniline, N,N-dimethyl-benzylamine, diazabicyclooctane (DABCO), diazabicyclononene (DBN), diazabicycloundecene (DBU), pyridine, 2-methyl-5-ethylpyridine and 4-dimethyl-aminopyridine.

The reaction temperatures can be varied within a substantial range in process (b). In general, the reaction is carried out between −80° C. and '100° C., preferably between −30° C. and +50° C. Process (b) according to the invention is in general carried out under normal pressure.

For carrying out process (b), in general between 1 and 2 moles, preferably between 1.0 and 1.2 moles, of benzene-1,2-disulphonic acid dichloride of the formula (III) and then between 1 and 100 moles, preferably between 5 and 50 moles, of water, and, if appropriate, between 1 and 3 moles, preferably between 1 and 2 moles, of a base are employed per mole of oxyguanidine derivative of the formula (IV).

The reaction components are usually brought together at room temperature or with external cooling and the reaction mixture is stirred until the reaction has ended.

Working up can be carried out in the customary manner; for example by a procedure in which the mixture is concentrated, if appropriate, and/or diluted with an organic solvent which is virtually water-immiscible, such as, for example, methylene chloride, washed with dilute hydrochloric acid and with water, dried, filtered and concentrated. The product of the formula (I) which remains in the residue is isolated by trituration with a suitable organic solvent, such as, for example, ethanol, made to crystallise and isolated by filtration with suction.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants;

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Argopyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

For the mixtures come known herbicides, such as, for example, N-(2-benzothiazolyl)-N,N'-dimethyl-urea, 3-(3-chloro-4-methylphenyl)-1,1-dimethylurea, 3-(4-isopropylphenyl)-1,1-dimethylurea, 4-amino-6-(1,1-dimethyl ethyl)-3-methylthio-1,2,4-triazin-5(4H)-one, 4-amino-6-(1,1-dimethyl ethyl)-3-ethylthio-1,2,4-triazin-5-(4H)-one, 1-amino-6-ethylthio-3-(2,2-dimethyl-propyl)-1,3,5-triazine-2,4-(1H,3H)-dione, 4-amino-3-methyl-6-phenyl-1,2,4-triazin-5(4H)-one, 2-chloro-4-ethylamino-6-isopropyl-amino-1,3,5-triazine, the R-enantiomer of (trimethylsilyl)-methyl 2-[4-(3,5-dichloropyridin-2-oxy)-phenoxy]-propionate, the R-enantiomer of (2-benzyloxy)-ethyl 2-[4-(3,5-dichloropyridyl-2-oxy)-phenoxy]-propionate, 2,4-dichlorophenoxyacetic acid, 2-(2,4-dichlorophenoxy)-propionic acid, 4-chloro-2-methylphenoxy-acetic acid, 2-(2-methyl-4-chloro-phenoxy)-propionic acid, 3,5-diiodo-4-hydroxy-benzonitrile, 3,5-dibromo-4-hydroxy-benzonitrile and diphenyl ethers and phenylpyridazines, such as, for example, pyridates. Surprisingly some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.001 and 15 kg of active compound per hectare of soil surface, preferably between 0.005 and 10 kg per ha.

The preparation and use of the active compounds according to the invention can be seen from the following examples.

PREPARATION EXAMPLES

Example 1

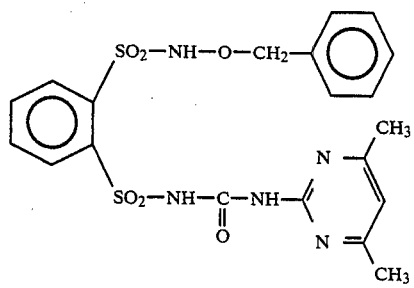

(Process (a))

A mixture of 21.9 g (0.05 mole) of the compound of the following structural formula

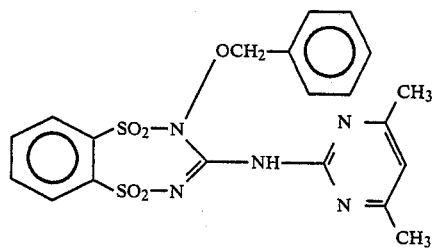

with 4 g (0.1 mole) of sodium hydroxide, 50 ml of water and 50 ml of dioxane is heated at 40° C. for 2 hours.

The mixture is then acidified with concentrated hydrochloric acid and the solution is concentrated to about half. The product obtained as crystals is filtered off with suction and dried. 12.5 g (54% of theory) of 1-(2-benzyloxyaminosulphonylphenylsulphonyl)-3-(4,6-dimethylpyrimidin-2-yl)-urea of melting point 186° C. (decomposition) are obtained.

Example 2

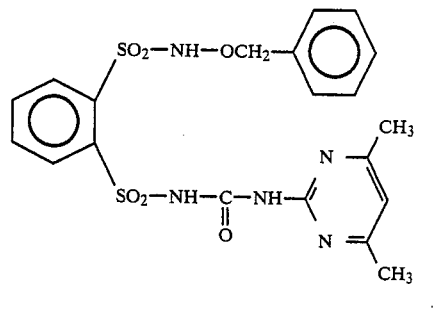

(Process (b))

14 g (0.05 mole) of benzene-1,2-disulphonic acid dichloride are added in portions to a mixture of 13.6 g (0.05 mole) of N'-(4,6-dimethylpyrimidin-2-yl)-N''-benzyloxyguanidine, 12 g (0.15 mole) of pyridine and 200 ml of methylene chloride at −20° C. The mixture is subsequently stirred at −20° C. for 3 hours and at +20° C. for 15 hours.

10 ml of water are then added to the reaction mixture and the mixture is stirred at 20° C. for a further 2 hours.

The methylene chloride solution is then washed with dilute hydrochloric acid and water and concentrated. The residue is triturated with ethanol; the product obtained as crystals is isolated by filtration with suction.

6.2 g (27% of theory) of 1(2-benzyloxyaminosulphonylphenylsulphonyl)-3-(4,6-dimethylpyrimidin-2-yl)-urea of melting point 188° C. (decomposition) are obtained.

The compounds of the formula (I) listed in the following Table 2 can also be prepared by the process described by way of example in the preceding Examples 1 and 2:

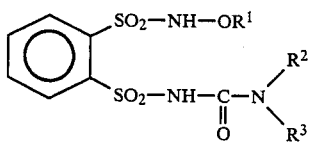 (I)

| Example No. | $R^1$ | $R^2$ | $R^3$ | Melting point (°C.) |
|---|---|---|---|---|
| 3 | —CH$_2$—CH═CH$_2$ | H | 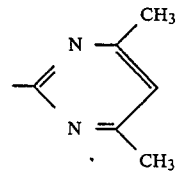 | 182 (decomp.) |

TABLE 2-continued

| Example No. | R¹ | R² | R³ | Melting point (°C.) |
|---|---|---|---|---|
| 4 | $-C_8H_{17}(-n)$ | H | ![N=C(CH3)-CH=C(CH3)-N=] ring | 145 |
| 5 | $-CH_2-C_6H_4-CH_3$ (p) | H | same diazadiene | |
| 6 | $-CH_2-C_6H_4-Cl$ (o) | H | same diazadiene | |
| 7 | $-CH_2-C_6H_4-COOC_2H_5$ (p) | H | same diazadiene | |
| 8 | $-CH_2-C_6H_4-NO_2$ (p) | H | same diazadiene | |
| 9 | $-CH_2CH_2-C_6H_5$ | H | same diazadiene | |
| 10 | $-CH_2-COOC_2H_5$ | H | same diazadiene | |
| 11 | $-CH(CH_3)-COOCH_3$ | H | same diazadiene | |

TABLE 2-continued
| Example No. | R[1] | R[2] | R[3] | Melting point (°C.) |
|---|---|---|---|---|
| 12 | —CH$_2$CH(CH$_3$)$_2$ | H | 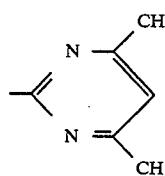 | |
| 13 | —CH$_3$ | CH$_3$ | 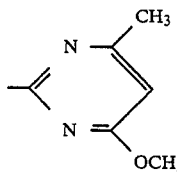 | |
| 14 | —CH$_3$ | H | 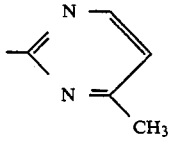 | 194–195 |
| 15 | —C$_2$H$_5$ | H | 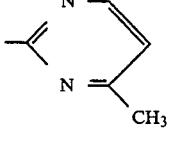 | |
| 16 | —CH$_2$—CH=CH$_2$ | H | 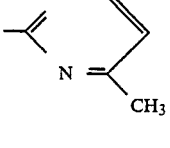 | |
| 17 | 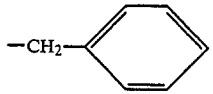 | H | 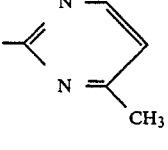 | |
| 18 | —CH$_2$COOC$_2$H$_5$ | H | 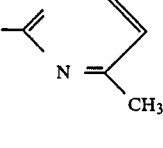 | |
| 19 | —CH$_2$CH(CH$_3$)$_2$ | H | 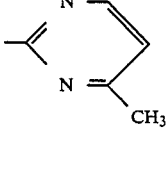 | |
| 20 | —CH$_3$ | H | 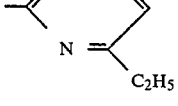 | |

TABLE 2-continued

| Example No. | R¹ | R² | R³ | Melting point (°C.) |
|---|---|---|---|---|
| 21 | —CH₃ | H | (pyrimidine with CH₃ and OCH₃) | 218 (decomp.) |
| 22 | —C₂H₅ | H | (pyrimidine with CH₃ and OCH₃) | |
| 23 | —C₃H₇ | H | (pyrimidine with CH₃ and OCH₃) | |
| 24 | —CH₂—CH=CH₂ | H | (pyrimidine with CH₃ and OCH₃) | |
| 25 | —CH₂CH(CH₃)₂ | H | (pyrimidine with CH₃ and OCH₃) | |
| 26 | —CH₂—C₆H₅ | H | (pyrimidine with CH₃ and OCH₃) | |
| 27 | —CH₃ | H | (pyrimidine with CH₃ and OC₂H₅) | |
| 28 | —CH₃ | H | (pyrimidine with Cl and OCH₃) | |

TABLE 2-continued
| Example No. | R¹ | R² | R³ | Melting point (°C.) |
|---|---|---|---|---|
| 29 | —C₂H₅ | H | 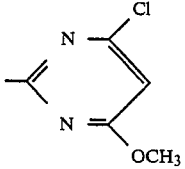 | |
| 30 | —CH₃ | H | 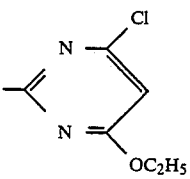 | |
| 31 | —CH₃ | H | 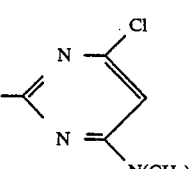 | |
| 32 | —CH₃ | H | 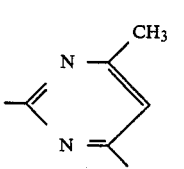 | |
| 33 | —CH₃ | H | 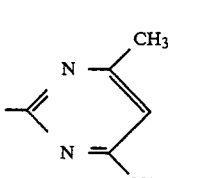 | |
| 34 | —CH₃ | H | 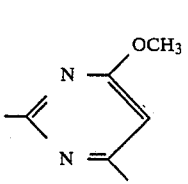 | |
| 35 | —C₂H₅ | H | 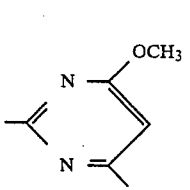 | |
| 36 | —C₃H₇ | H | 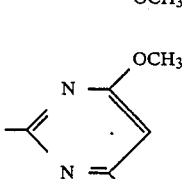 | |

TABLE 2-continued

| Example No. | R¹ | R² | R³ | Melting point (°C.) |
|---|---|---|---|---|
| 37 | —CH₂—CH=CH₂ | H | pyrimidine with OCH₃, OCH₃ | |
| 38 | —CH₂CH(CH₃)₂ | H | pyrimidine with OCH₃, OCH₃ | |
| 39 | —CH₂—C₆H₅ | H | pyrimidine with OCH₃, OCH₃ | |
| 40 | —C₄H₉ | H | pyrimidine with OCH₃, OCH₃ | |
| 41 | —CH₃ | H | pyrimidine with OCH₃, OCHF₂ | |
| 42 | —C₂H₅ | H | pyrimidine with OCH₃, OCHF₂ | |
| 43 | —CH₃ | H | pyrimidine with OC₂H₅, OC₂H₅ | |
| 44 | —CH₃ | H | pyrimidine with CH₃, CH₃ | |
| 45 | —CH₃ | H | pyrimidine with CH₃, OCH₂CF₃ | |

TABLE 2-continued

| Example No. | R¹ | R² | R³ | Melting point (°C.) |
|---|---|---|---|---|
| 46 | —CH₂—C₆H₅ | H | pyrimidin-2-yl | |
| 47 | —CH₃ | H | 4,6-dimethylpyridin-2-yl | |
| 48 | —CH₃ | H | 4-methyl-5-(methoxycarbonyl)pyrimidin-2-yl | |
| 49 | —C₂H₅ | H | 4,6-dimethylpyrimidin-2-yl | 218 |
| 50 | —C₃H₇(—n) | H | 4,6-dimethylpyrimidin-2-yl | 212 (decomp.) |
| 51 | —C₃H₇(—i) | H | 4,6-dimethylpyrimidin-2-yl | 218 (decomp.) |
| 52 | —C₄H₉(—n) | H | 4,6-dimethylpyrimidin-2-yl | 109 |
| 53 | —CH₃ | H | 4,6-dimethylpyrimidin-2-yl | 218 |

Example 54

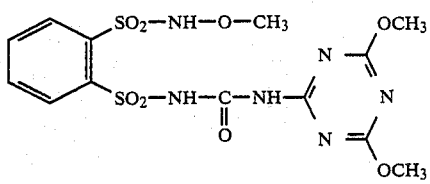

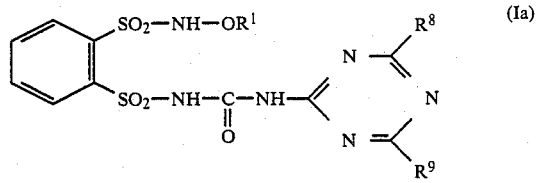

(Process (a))

5 ml of concentrated hydrochloric acid are added to a mixture of 4.3 g (0.01 mole) of the compound of the following structural formula

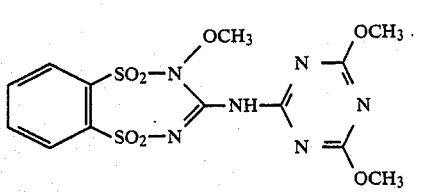

and 40 ml of water, with vigorous stirring. Stirring is continued at 20° to 30° C. for 2 hours and the precipitate formed is then filtered off with suction.

After drying, 3.9 g (87% of theory) of 1-(2-methoxyaminosulphonylphenylsulphonyl)-3-(4,6-dimethoxy-1,3,5-triazin-2-yl)-urea of melting point 162° C. (decomposition) are obtained.

Example 55

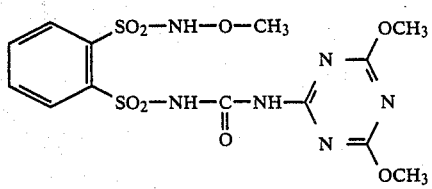

(Process (b))

7.1 g (0.025 mole) of benzene-1,2-disulphonic acid chloride are added in portions to a mixture of 5.6 g (0.025 mole) of N'-(4,6-dimethoxy-1,3,5-triazin-2-yl)-N''-methoxy-guanidine and 50 ml of pyridine at −10° C. The mixture is stirred at −10° C. for 3 hours and then at 20°–25° C. for 12 hours. The solvent is then stripped off and the residue is taken up in 200 ml of water. The mixture is filtered. The filtrate is acidified with concentrated hydrochloric acid. After about 1 hour, the precipitate formed is filtered off with suction, washing with methanol and then dried.

6.1 g (54% of theory) of 1-(2-methoxyaminosulphonylphenylsulphonyl)-3-(4,6-dimethoxy-1,3,5-triazin-2-yl)-urea of melting point 160° C. are obtained.

The compounds of the formula (Ia) listed in the following Table 2a can also be prepared by the processes described by way of example in the preceding Examples 54 and 55:

TABLE 2a

| Example No. | $R^1$ | $R^8$ | $R^9$ | Melting point [°C.] |
|---|---|---|---|---|
| 56 | —$C_2H_5$ | —$OCH_3$ | —$OCH_3$ | |
| 57 | —$CH_2$—CH=$CH_2$ | —$OCH_3$ | —$OCH_3$ | |
| 58 | —$CH_3$ | —$OCH_3$ | —$OC_2H_5$ | |
| 59 | —$C_4H_9$ | —$OCH_3$ | —$OC_2H_5$ | |
| 60 | —$CH_3$ | —$OCH_3$ | —$N(C_2H_5)_2$ | |
| 61 | —$C_3H_7$—n | —$SCH_3$ | —$NHC_2H_5$ | |
| 62 | —$CH_3$ | —$CH_3$ | —$OCH_3$ | 174 |
| 63 | —$C_8H_{17}$—n | —$CH_3$ | —$OCH_3$ | |
| 64 | —$CH_2$—C$_6$H$_5$ | —$CH_3$ | —$OCH_3$ | 177 |
| 65 | —$CH_3$ | —$OCH_3$ | —$SCH_3$ | |
| 66 | —$CH_3$ | —$CH_3$ | —$OC_2H_5$ | 201 |
| 67 | —$CH_2$—C$_6$H$_5$ | —$CH_3$ | —$OC_2H_5$ | 212 |
| 68 | —$CH_3$ | —$SCH_3$ | —$NHC_2H_5$ | |
| 69 | —$CH_3$ | —$C_2H_5$ | —$OCH_3$ | |
| 70 | —$CH_3$ | —$CH_3$ | —$CH_3$ | >240 |
| 71 | —$CH_2$—CH=$CH_2$ | —$CH_3$ | —$CH_3$ | |
| 72 | —$CH_2$—CH($CH_3$)$_2$ | —$CH_3$ | —$OC_2H_5$ | 156 |
| 73 | —$CH_2$—CH($CH_3$)$_2$ | —$CH_3$ | —$OCH_3$ | 176 |
| 74 | —CH($CH_3$)$_2$ | —$CH_3$ | —$OC_2H_5$ | 183 |
| 75 | —CH($CH_3$)$_2$ | —$OC_2H_5$ | —$NHCH_3$ | 208 |
| 76 | —$CH_3$ | —$OCH_3$ | —$NHCH_3$ | 197 |
| 77 | —$CH_2$—C$_6$H$_5$ | —$OC_2H_5$ | —$NHCH_3$ | 197 |
| 78 | —CH($CH_3$)$_2$ | —$CH_3$ | —$OCH_3$ | 192 |
| 79 | —$CH_3$ | —$OC_2H_5$ | —$NHCH_3$ | 215 |
| 80 | —$CH_2$—C$_6$H$_5$ | —$OCH_3$ | —$OCH_3$ | 155 |
| 81 | —$CH_3$ | —$CH_3$ | —$N(CH_3)_2$ | 182 |
| 82 | —$CH_2$—(2,4-Cl$_2$C$_6$H$_3$) | —$CH_3$ | —$CH_3$ | 154 |
| 83 | —$CH_3$ | —$CH_3$ | —$SCH_3$ | |
| 84 | —$CH_2CH(CH_3)_2$ | —$CH_3$ | —$N(CH_3)_2$ | 170 |
| 85 | —$CH_3$ | —$CH_3$ | —$NHCH_3$ | 202 |
| 86 | —CH($CH_3$)$_2$ | —$CH_3$ | —$NHCH_3$ | 267 |
| 87 | —$CH_2CH(CH_3)_2$ | —$CH_3$ | —$NHCH_3$ | |
| 88 | —$CH_3$ | —$CH_3$ | —$NHC_2H_5$ | |

TABLE 2a-continued

| Example No. | R¹ | R⁸ | R⁹ | Melting point [°C.] |
|---|---|---|---|---|
| 89 | —CH(CH₃)₂ | —CH₃ | —NHC₂H₅ | |
| 90 | —CH₂CH(CH₃)₂ | —CH₃ | —NHC₂H₅ | |

PREPARATION OF THE STARTING COMPOUNDS OF THE FORMULA (II)

Example (II-1)

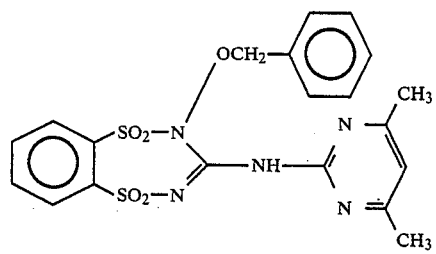

14 g (0.05 mole) of benzene-1,2-disulphonic acid dichloride are added in portions to a mixture of 13.6 g (0.05 mole) of N'-(4,6-dimethylpyrimidin-2-yl)-N''-benzyloxy-guanidine, 12 g (0.15 mole) of pyridine and 100 ml of methylene chloride at −20° C. The mixture is subsequently stirred at −20° C. for 3 hours and at +20° C. for 15 hours.

The reaction mixture is then evaporated and 70 ml of dioxane are added to the residue. The mixture is filtered. The filtrate is concentrated, the residue is triturated with ethanol and the product which has precipitated is isolated by filtration with suction.

15 g (68% of theory) of the compound of the above-mentioned structural formula of melting point 199° C. are obtained.

The compounds of the formula (II) listed in the following Table 3 can be prepared by the process described by way of example in the preceding example:

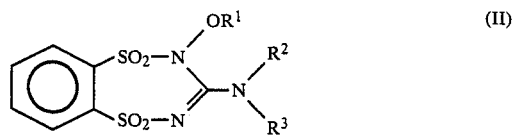

TABLE 3

| Example No. | R¹ | R² | R³ | Melting point (°C.) |
|---|---|---|---|---|
| (II-2) | —CH₂—CH=CH₂ | H | 4,6-dimethylpyrimidin-2-yl | 180 (decomp.) |
| (II-3) | —C₈H₁₇(—n) | H | 4,6-dimethylpyrimidin-2-yl | 164 |
| (II-4) | —CH₂—COOC₂H₅ | H | 4,6-dimethylpyrimidin-2-yl | 210 (decomp.) |
| (II-5) | —CH₂—C₆H₄—CH₃ (p) | H | 4,6-dimethylpyrimidin-2-yl | |
| (II-6) | —CH₂—C₆H₄—Cl (o) | H | 4,6-dimethylpyrimidin-2-yl | |

TABLE 3-continued

| Example No. | R¹ | R² | R³ | Melting point (°C.) |
|---|---|---|---|---|
| (II-7) | -CH₂-C₆H₄-COOC₂H₅ (para) | H | 4,6-dimethylpyrimidin-2-yl | |
| (II-8) | -CH₂CH₂-C₆H₄-CH₃ (para) | H | 4,6-dimethylpyrimidin-2-yl | |
| (II-9) | -CH₂-C₆H₄-NO₂ (para) | H | 4,6-dimethylpyrimidin-2-yl | |
| (II-10) | -CH(CH₃)-COOCH₃ | H | 4,6-dimethylpyrimidin-2-yl | |
| (II-11) | -CH₂-CH(CH₃)₂ | H | 4,6-dimethylpyrimidin-2-yl | amorphous |
| (II-12) | -CH₃ | CH₃ | 4-methyl-6-methoxypyrimidin-2-yl | |
| (II-13) | -CH₃ | C₂H₅ | 4-methyl-6-ethoxypyrimidin-2-yl | |
| (II-14) | -CH₃ | H | 4-methylpyrimidin-2-yl | |
| (II-15) | -CH₂CH(CH₃)₂ | H | 4-methylpyrimidin-2-yl | |

TABLE 3-continued

| Example No. | R¹ | R² | R³ | Melting point (°C.) |
|---|---|---|---|---|
| (II-16) | —CH₂—C₆H₅ | H | 2-methyl-6-methyl-pyrimidin-4-yl | |
| (II-17) | —CH₂—COOC₂H₅ | H | 2-methyl-6-methyl-pyrimidin-4-yl | |
| (II-18) | —CH₃ | H | 5-methyl-2-methyl-6-methoxy-pyrimidin-4-yl | 151 (decomp.) |
| (II-19) | —C₂H₅ | H | 5-methyl-2-methyl-6-methoxy-pyrimidin-4-yl | |
| (II-20) | —C₃H₇ | H | 5-methyl-2-methyl-6-methoxy-pyrimidin-4-yl | |
| (II-21) | —CH₂—CH=CH₂ | H | 5-methyl-2-methyl-6-methoxy-pyrimidin-4-yl | |
| (II-22) | —CH₂CH(CH₃)₂ | H | 6-methyl-2-methyl-5-methoxy-pyrimidin-4-yl | |
| (II-23) | —CH₂—C₆H₅ | H | 6-methyl-2-methyl-5-methoxy-pyrimidin-4-yl | |
| (II-24) | —CH₃ | H | 6-methyl-2-methyl-5-ethoxy-pyrimidin-4-yl | |

TABLE 3-continued

| Example No. | R¹ | R² | R³ | Melting point (°C.) |
|---|---|---|---|---|
| (II-25) | —CH₃ | H | 2-methyl-4-chloro-6-methoxypyrimidinyl-5-vinyl | |
| (II-26) | —CH₃ | H | 2-methyl-4-chloro-6-ethoxypyrimidinyl-5-vinyl | |
| (II-27) | —CH₃ | H | 2-methyl-4-chloro-6-dimethylaminopyrimidinyl-5-vinyl | |
| (II-28) | —CH₃ | H | 2,4-dimethyl-6-methylthiopyrimidinyl-5-vinyl | |
| (II-29) | —CH₃ | H | 2,4-dimethyl-6-dimethylaminopyrimidinyl-5-vinyl | |
| (II-30) | —CH₃ | H | 2,4-dimethyl-5-acetylpyrimidinyl-... | |
| (II-31) | —CH₃ | H | 2,4-dimethyl-5-methoxycarbonylpyrimidinyl-... | |
| (II-32) | —CH₃ | H | 2-methyl-4,6-dimethoxypyrimidinyl-5-vinyl | |
| (II-33) | —C₂H₅ | H | 2-methyl-4,6-dimethoxypyrimidinyl-5-vinyl | |

TABLE 3-continued
| Example No. | R¹ | R² | R³ | Melting point (°C.) |
|---|---|---|---|---|
| (II-34) | —C₃H₇(—n) | H | 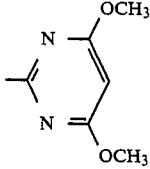 | |
| (II-35) | —C₄H₉(—n) | H | 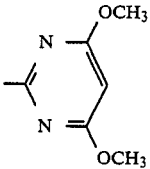 | |
| (II-36) | —CH₂—C₆H₅ | H | 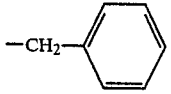 | |
| (II-37) | —CH₂—CH=CH₂ | | 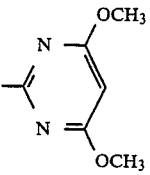 | |
| (II-38) | —CH₂CH(CH₃)₂ | H | 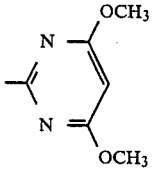 | |
| (II-39) | —CH₃ | H | 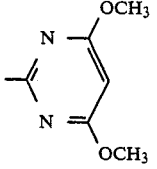 | |
| (II-40) | —CH₂—C₆H₅ | H | 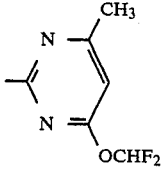 | |
| (II-41) | —CH₃ | H | 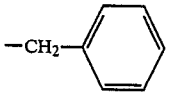 | |
| (II-42) | —CH₃ | H | 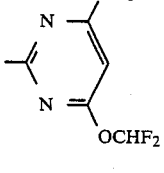 | |

TABLE 3-continued

| Example No. | R¹ | R² | R³ | Melting point (°C.) |
|---|---|---|---|---|
| (II-43) | —CH₃ | H | 2-methyl-6-(trifluoromethoxy)-pyrimidin-4-yl (with CH₃ at 4-position and OCH₂F₃ at 6-position) | |
| (II-44) | —CH₂CH(CH₃)₂ | H | pyrimidin-4-yl | |
| (II-45) | —CH₃ | H | 4,6-dimethylpyrimidin-2-yl | |
| (II-46) | —CH₃ | H | 4,6-dimethylpyrimidin-2-yl | 158 |
| (II-47) | —C₂H₅ | H | 4,6-dimethylpyrimidin-2-yl | 104 |
| (II-48) | —C₃H₇(—n) | H | 4,6-dimethylpyrimidin-2-yl | 134 |
| (II-49) | —C₄H₉(—n) | H | 4,6-dimethylpyrimidin-2-yl | 179 |
| (II-50) | —CH₃ | H | pyrimidin-2-yl | 187 |

PREPARATION OF FURTHER STARTING COMPOUNDS OF THE FORMULA (II)

Example (II-51)

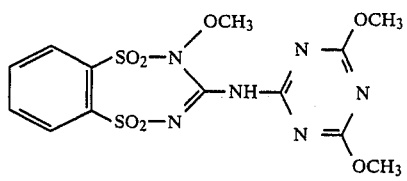

7.1 g (0.025 mole) of benzene-1,2-disulphonic acid chloride are added in portions to a mixture of 5.6 g (0.025 mole) of N'-(4,6-dimethoxy-1,3,5-triazin-2-yl)-N''-methoxy-guanidine, 6 g (0.025 mole) of DABCO and 60 ml of methylene chloride at −10° C. The mixture is subsequently stirred at 0° to −5° C. for 15 hours. The reaction mixture is then washed with ice-cold dilute hydrochloric acid and ice-water. The methylene chloride solution is dried and concentrated.

After incipient distillation, 4.6 g (43% of theory) of the compound of the abovementioned structural formula are obtained in the form of an amorphous mass.

The substance is characterized by the $H^1$—NMR spectrum.

The compounds of the formula (IIa) listed in the following Table 3a can be prepared by the process described by way of example in the preceding example (II-51):

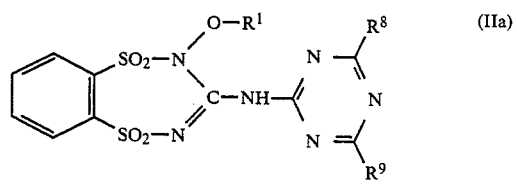

TABLE 3a

| Example No. | $R^1$ | $R^8$ | $R^9$ | Melting point (°C.) |
|---|---|---|---|---|
| II-52 | —$C_2H_5$ | —$OCH_3$ | —$OCH_3$ | |
| II-53 | —$CH_2$—CH=$CH_2$ | —$OCH_3$ | —$OCH_3$ | |
| II-54 | —$CH_3$ | —$OCH_3$ | —$OC_2H_5$ | |
| II-55 | —$C_4H_9$—n | —$OCH_3$ | —$OC_2H_5$ | |
| II-56 | —$CH_3$ | —$OCH_3$ | —$N(C_2H_5)_2$ | |
| II-57 | —$C_3H_7$—n | —$SCH_3$ | —$NHC_2H_5$ | |
| II-58 | —$CH_3$ | —$CH_3$ | —$OCH_3$ | amorphous |
| II-59 | —$C_8H_{17}$—n | —$CH_3$ | —$OCH_3$ | |
| II-60 | —$CH_2$—C₆H₅ | —$OCH_3$ | —$OCH_3$ | |
| II-61 | —$CH_3$ | —$OCH_3$ | —$SCH_3$ | |
| II-62 | —$CH_3$ | —$CH_3$ | —$OC_2H_5$ | |
| II-63 | —$CH_2$—C₆H₅ | —$CH_3$ | —$OC_2H_5$ | amorphous |
| II-64 | —$CH_3$ | —$SCH_3$ | —$NHC_2H_5$ | |
| II-65 | —$CH_3$ | —$C_2H_5$ | —$OCH_3$ | |
| II-66 | —$CH_3$ | —$CH_3$ | —$CH_3$ | amorphous |
| II-67 | —$CH_2$—CH=$CH_2$ | —$CH_3$ | —$CH_3$ | |
| II-68 | —$CH_2$—C₆H₅ | —$CH_3$ | —$OC_2H_5$ | amorphous |
| II-69 | —$CH_3$ | —$SCH_3$ | —$NHC_2H_5$ | |
| II-70 | —$CH_3$ | —$C_2H_5$ | —$OCH_3$ | |
| II-71 | —$CH_3$ | —$CH_3$ | —$CH_3$ | |
| II-72 | —$CH_2$—CH=$CH_2$ | —$CH_3$ | —$CH_3$ | amorphous |
| II-73 | —$CH_2$—C₆H₄—$COOC_2H_5$ | —$CH_3$ | —$CH_3$ | 195 |
| II-74 | —CH($CH_3)_2$ | —$CH_3$ | —$OCH_3$ | amorphous |
| II-75 | —CH($CH_3)_2$ | —$CH_3$ | —$OC_2H_5$ | amorphous |
| II-76 | —$(CH_2)_7$—$CH_3$ | —$OCH_3$ | —$OCH_3$ | 110 |

TABLE 3a-continued

| Example No. | R¹ | R⁸ | R⁹ | Melting point (°C.) |
|---|---|---|---|---|
| II-77 | —CH₂—C₆H₅ | —OCH₃ | —OCH₃ | 185 |
| II-78 | —CH₂—(2,6-dichlorophenyl) | —CH₃ | —CH₃ | 150 |

PREPARATION OF THE STARTING SUBSTANCES OF THE FORMULA (IV)

Example (IV-1)

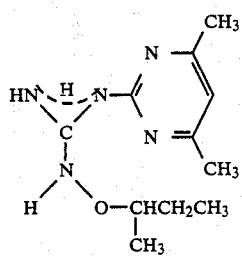

A mixture of 143 g (0.97 mole) of 2-cyanoamino-4,6-dimethyl-pyrimidine, 94.3 g (1.06 moles) of O-sec.-butyl-hydroxylamine and 190 ml of ethanol is heated at the boiling point under reflux for 6 hours. The mixture is then filtered with suction, the filtrate is concentrated and 500 ml of water are added to the residue. The product thereby obtained as crystals is isolated by filtration with suction.

131 g (57% of theory) of N'-(4,6-dimethyl-pyrimidin-2-yl)-N''-sec.-butoxy-guanidine of melting point 78° C. are obtained.

The compounds of the formula (IV) listed in the following Table 4 can be prepared analogously:

TABLE 4

| Example No. | R¹ | R² | R³ | Melting point (°C.) |
|---|---|---|---|---|
| (IV-2) | —CH₂—C₆H₄—CH₃ (para) | H | 4,6-dimethyl-pyrimidin-2-yl | 85–86 |
| (IV-3) | —CH₂—C₆H₄—Cl (ortho) | H | 4,6-dimethyl-pyrimidin-2-yl | 102–103 |
| (IV-4) | —CH₂—C₆H₄—NO₂ (para) | H | 4,6-dimethyl-pyrimidin-2-yl | 170–172 |
| (IV-5) | —CH₂—CH₂—C₆H₅ | H | 4,6-dimethyl-pyrimidin-2-yl | $n_D^{24.5} = 1.5776$ |

TABLE 4-continued

| Example No. | R¹ | R² | R³ | Melting point (°C.) |
|---|---|---|---|---|
| (IV-6) | —CH₂—CH=CH₂ | H | 2-methyl-4,6-dimethylpyrimidinyl vinyl group | 103 |
| (IV-7) | —C₈H₁₇(—n) | H | 2-methyl-4,6-dimethylpyrimidinyl vinyl group | 58 |
| (IV-8) | —CH₂—COOC₂H₅ | H | 2-methyl-4,6-dimethylpyrimidinyl vinyl group | 98–99 |
| (IV-9) | —CH—COOCH₃<br>  \|<br>  CH₃ | H | 2-methyl-4,6-dimethylpyrimidinyl vinyl group | 147–148 |
| (IV-10) | —CH₃ | —CH₃ | 2-methyl-4,6-dimethylpyrimidinyl vinyl group | 95 |
| (IV-11) | —CH₂CH(CH₃)₂ | H | 2-methyl-4,6-dimethylpyrimidinyl vinyl group | 52 |
| (IV-12) | phenyl | H | 2-methyl-4,6-dimethylpyrimidinyl vinyl group | 189–192 (decomp.) |
| (IV-13) | —CH₂CH₂CH₂Cl | H | 2-methyl-4,6-dimethylpyrimidinyl vinyl group | 137 |

TABLE 4-continued
| Example No. | R¹ | R² | R³ | Melting point (°C.) |
|---|---|---|---|---|
| (IV-14) | —CH₂COOCH₃ | H | 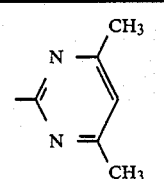 | 148–149 |
| (IV-15) | 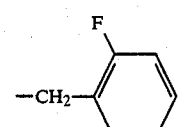 | H | 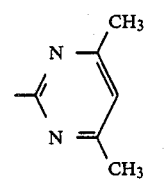 | 114–116 |
| (IV-16) | 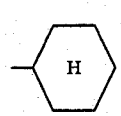 | H | 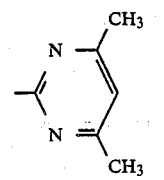 | |
| (IV-17) | 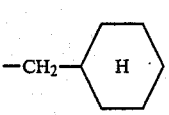 | H | 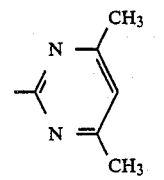 | |
| (IV-18) | —CH₂—CO—N(CH₃)₂ | H | 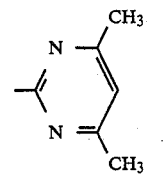 | |
| (IV-19) | —CH₂OCH₃ | H | 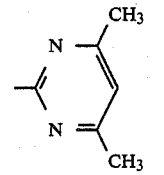 | |
| (IV-20) | —CH₂SCH₃ | H | 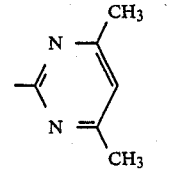 | |
| (IV-21) | 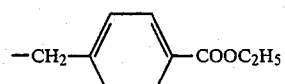 | H | 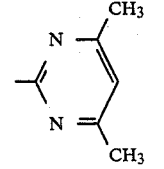 | 138 |

TABLE 4-continued

| Example No. | R¹ | R² | R³ | Melting point (°C.) |
|---|---|---|---|---|
| (IV-22) | —CH₂CH₂OCH₃ | H | 4,6-dimethylpyrimidin-2-yl | |
| (IV-23) | —CH₂CF₃ | H | 4,6-dimethylpyrimidin-2-yl | |
| (IV-24) | —CH₂-(2,6-dichlorophenyl) | H | 4,6-dimethylpyrimidin-2-yl | 152 |
| (IV-25) | —CH₂-phenyl | H | 4,6-dimethylpyrimidin-2-yl | 102 |
| (IV-26) | —CH₂—COOCH(CH₃)₂ | H | 4,6-dimethylpyrimidin-2-yl | 112 |
| (IV-27) | —CH₃ | H | 4-methylpyrimidin-2-yl | 152 |
| (IV-28) | —C₂H₅ | H | 4-methylpyrimidin-2-yl | 95 |
| (IV-29) | —C₃H₇(—n) | H | 4-methylpyrimidin-2-yl | |
| (IV-30) | —CH(CH₃)₂ | H | 4-methylpyrimidin-2-yl | |

TABLE 4-continued

| Example No. | R¹ | R² | R³ | Melting point (°C.) |
|---|---|---|---|---|
| (IV-31) | —C₄H₉(—n) | H | 2-methyl-6-methylpyrimidin-4-yl vinyl | |
| (IV-32) | —CH₂CH(CH₃)₂ | H | 2-methyl-6-methylpyrimidin-4-yl vinyl | |
| (IV-33) | —CH₂—CH=CH₂ | H | 2-methyl-6-methylpyrimidin-4-yl vinyl | |
| (IV-34) | —CH₂—C₆H₅ | H | 2-methyl-6-methylpyrimidin-4-yl vinyl | 150 |
| (IV-35) | —CH₂—COOC₂H₅ | H | 2-methyl-6-methylpyrimidin-4-yl vinyl | |
| (IV-36) | —CH₃ | H | 2-methyl-6-ethylpyrimidin-4-yl vinyl | 98 |
| (IV-37) | —CH₃ | H | 2-methyl-5-methyl-6-methoxypyrimidin-4-yl vinyl | 126 |
| (IV-38) | —CH₂—C₆H₅ | H | 2-methyl-5-methyl-6-methoxypyrimidin-4-yl vinyl | (amorphous) |
| (IV-39) | —C₂H₅ | H | 2-methyl-5-methyl-6-methoxypyrimidin-4-yl vinyl | (amorphous) |

TABLE 4-continued

| Example No. | R¹ | R² | R³ | Melting point (°C.) |
|---|---|---|---|---|
| (IV-40) | —C₃H₇ | H | 4-methyl-6-methoxy-2-methylpyrimidinyl vinyl | |
| (IV-41) | —CH₂CH(CH₃)₂ | H | 4-methyl-6-methoxy-2-methylpyrimidinyl vinyl | |
| (IV-42) | —CH₂—CH=CH₂ | H | 4-methyl-6-methoxy-2-methylpyrimidinyl vinyl | |
| (IV-43) | —CH₃ | H | 4-methyl-6-ethoxy-2-methylpyrimidinyl vinyl | |
| (IV-44) | —CH₃ | CH₃ | 4-methyl-6-methoxy-2-methylpyrimidinyl vinyl | 135 |
| (IV-45) | —CH₃ | C₂H₅ | 4-methyl-6-ethoxy-2-methylpyrimidinyl vinyl | |
| (IV-46) | —CH₃ | H | 4-chloro-6-methoxy-2-methylpyrimidinyl vinyl | 112 |
| (IV-47) | —CH₂—C₆H₅ | H | 4-chloro-6-methoxy-2-methylpyrimidinyl vinyl | |

TABLE 4-continued

| Example No. | $R^1$ | $R^2$ | $R^3$ | Melting point (°C.) |
|---|---|---|---|---|
| (IV-48) | —CH$_3$ | H | 4-chloro-6-ethoxypyrimidin-2-yl (vinylene-linked) | |
| (IV-49) | —CH$_3$ | H | 4-chloro-6-dimethylamino-pyrimidin-2-yl | |
| (IV-50) | —CH$_3$ | H | 4-methyl-6-methylthio-pyrimidin-2-yl | |
| (IV-51) | —CH$_3$ | H | 4-methyl-6-dimethylamino-pyrimidin-2-yl | |
| (IV-52) | —CH$_3$ | H | 4,6-dimethoxypyrimidin-2-yl | 122 |
| (IV-53) | —C$_2$H$_5$ | H | 4,6-dimethoxypyrimidin-2-yl | |
| (IV-54) | —C$_3$H$_7$ | H | 4,6-dimethoxypyrimidin-2-yl | |
| (IV-55) | —C$_4$H$_9$ | H | 4,6-dimethoxypyrimidin-2-yl | |

TABLE 4-continued
| Example No. | R¹ | R² | R³ | Melting point (°C.) |
|---|---|---|---|---|
| (IV-56) | —CH₂CH(CH₃)₂ | H | 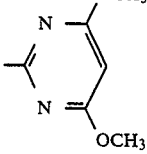 | 76 |
| (IV-57) | —CH—CH₂CH₃<br>   \|<br>   CH₃ | H | 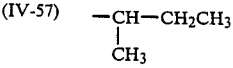 | 68 |
| (IV-58) | —CH₂—C₆H₅ | H | 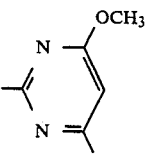 | 74 |
| (IV-59) | —CH₂—COOC₂H₅ | H | 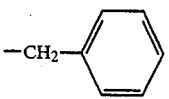 | |
| (IV-60) | —CH₃ | H | 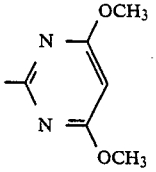 | |
| (IV-61) | —CH₃ | H | 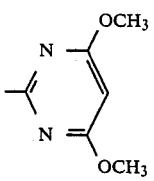 | 107–109 |
| (IV-62) | —CH₃ | H | 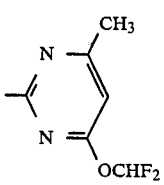 | |
| (IV-63) | —CH₂—C₆H₅ | H | 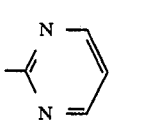 | 112 |
| (IV-64) | —CH(C₆H₅)₂ | H | 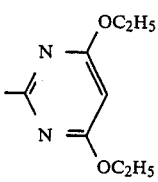 | 165 |

TABLE 4-continued

| Example No. | $R^1$ | $R^2$ | $R^3$ | Melting point (°C.) |
|---|---|---|---|---|
| (IV-65) | —CH$_2$—C$_6$H$_5$ | H | 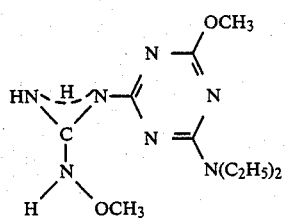 | 130 |

PREPARATION OF FURTHER STARTING COMPOUNDS OF THE FORMULA (IV)

Example (IV-66)

A mixture of 66.5 g (0.3 mole) of 2-cyanamino-4-diethylamino-6-methoxy-s-triazine, 50 g (0.8 mole) of O-methyl-hydroxylamine hydrochloride and 300 ml of ethanol is heated at the boiling point under reflux for 15 hours. It is then filtered, the filtrate is concentrated, the residue is taken up in about 200 ml of water, the mixture is rendered alkaline with sodium hydroxide solution and the product thereby obtained as crystals is isolated by filtration with suction.

35.0 g (43% of theory) of N'-(4-diethylamino-6-methoxy-s-triazin-2-yl)-N''-methoxy-guanidine of melting point 112° C. are obtained.

The compounds of the formula (IVa) listed in the following Table 4a can be prepared analogously:

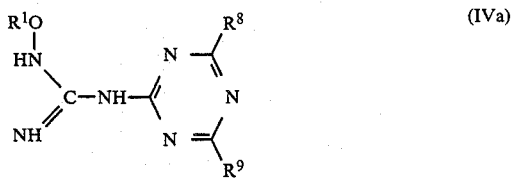 (IVa)

TABLE 4a

| Example No. | $R^1$ | $R^8$ | $R^9$ | Melting point [°C.] |
|---|---|---|---|---|
| IV-67 | —CH$_3$ | —SCH$_3$ | —NHC$_2$H$_5$ | 117 |
| IV-68 | —CH$_3$ | —SCH$_3$ | —NHCH$_3$ | |
| IV-69 | —CH$_3$ | —Cl | —N(C$_2$H$_5$)$_2$ | |
| IV-70 | —C$_2$H$_5$ | —OCH$_3$ | —N(C$_2$H$_5$)$_2$ | |
| IV-71 | —C$_3$H$_7$—n | —SCH$_3$ | —NHC$_2$H$_5$ | |
| IV-72 | —CH(CH$_3$)$_2$ | —OCH$_3$ | —NHCH$_3$ | |
| IV-73 | —CH$_2$—CH=CH$_2$ | —OCH$_3$ | —N(CH$_3$)$_2$ | |
| IV-74 | —C$_4$H$_9$—n | —OCH$_3$ | —N(CH$_3$)$_2$ | |
| IV-75 | —CH$_2$—C$_6$H$_5$ | —OCH$_3$ | —N(CH$_3$)$_2$ | |
| IV-76 | —CH$_2$COOC$_2$H$_5$ | —OCH$_3$ | —N(CH$_3$)$_2$ | |
| IV-77 | —CH$_2$—C$_6$H$_4$—CH$_3$ | —OCH$_3$ | —N(CH$_3$)$_2$ | |
| IV-78 | —CH$_3$ | —CH$_3$ | —OCH$_3$ | 126 |
| IV-79 | —CH$_2$—C$_6$H$_5$ | —CH$_3$ | —OCH$_3$ | 112 |
| IV-80 | —C$_8$H$_{17}$ | —CH$_3$ | —OCH$_3$ | 95 |
| IV-81 | —CH$_2$—C$_6$H$_5$ | —SCH$_3$ | —NHC$_2$H$_5$ | 122 |
| IV-82 | —CH$_3$ | —CH$_3$ | —OC$_2$H$_5$ | |

TABLE 4a-continued

| Example No. | R¹ | R⁸ | R⁹ | Melting point [°C.] |
|---|---|---|---|---|
| IV-83 | —CH₂—C₆H₅ | —CH₃ | —OC₂H₅ | $n_D^{21} = 1.5824$ |
| IV-84 | —CH₃ | —CH₃ | —CH₃ | 112 |
| IV-85 | —CH₂—C₆H₅ | —CH₃ | —CH₃ | |
| IV-86 | —CH₂—CH=CH₂ | —CH₃ | —CH₃ | |
| IV-87 | —CH₃ | —OCH₃ | —OCH₃ | 107 |
| IV-88 | —CH₂—C₆H₅ | —OCH₃ | —OCH₃ | 127 |
| IV-89 | —CH₂—C(CH₃)₃ | —CH₃ | —CH₃ | |
| IV-90 | —CH₂CH₂—OCH₃ | —OCH₃ | —OCH₃ | |
| IV-91 | —CH₂CH₂—OC₂H₅ | —CH₃ | —OCH₃ | |
| IV-92 | —CH₂CH₂—SCH₃ | —CH₃ | —OC₂H₅ | |
| IV-93 | —CH₂CH₂—SC₂H₅ | —CH₃ | —CH₃ | |
| IV-94 | —CH₂—CONH₂ | —OCH₃ | —OCH₃ | |
| IV-95 | —CH₂—CH=CHCl | —CH₃ | —OCH₃ | |
| IV-96 | —CH(C₆H₅)₂ | —CH₃ | —CH₃ | |
| IV-97 | —C(C₆H₅)₃ | —CH₃ | —CH₃ | |
| IV-98 | —CH₃ | —C₂H₅ | —OCH₃ | |
| IV-99 | —CH₃ | —SCH₃ | —OCH₃ | |
| IV-100 | —CH₃ | —OC₂H₅ | —OCH₃ | |
| IV-101 | —CH₃ | —NH—C₂H₅ | —OCH₃ | |
| IV-102 | —CH₃ | —N(CH₃)₂ | —OCH₃ | |
| IV-103 | —CH₃ | —CH₃ | —SCH₃ | |
| IV-104 | —CH₃ | —NH—CH₃ | —CH₃ | |
| IV-105 | —CH₃ | N(CH₃)₂ | —CH₃ | |

PREPARATION OF THE STARTING SUBSTANCES OF THE FORMULA (V)

Example (V-1)

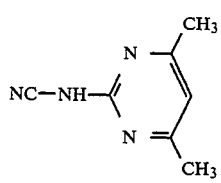

A mixture of 42 g (0.5 mole) of cyanoguanidine ("dicyandiamide") and 50 g (0.5 mole) of 2,4-pentanedione ("acetylacetone") is heated at 120° C. for 15 hours. After cooling, 500 ml of water are then added to the reaction mixture and the solution is acidified with hydrochloric acid at 0° C. to 10° C. The product thereby obtained as crystals is isolated by filtration with suction. 51.8 g (70% of theory) of 2-cyanoamino-4,6-dimethyl-pyrimidine of melting point 205° C. are obtained.

Example (V-2)

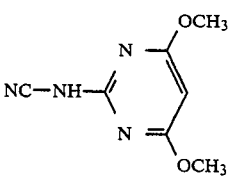

A solution, heated to 100° C., of 24 g (0.427 mole) of potassium hydroxide in 100 ml of water is added to a mixture of 9.2 g (0.043 mole) of 4,6-dimethoxypyrimidin-2-yl-thiourea and 70 ml of water at 100° C., with stirring. The mixture is subsequently stirred at 100° C. for 2 minutes and a solution, warmed to 100° C., of 16.2 g (0.05 mole) of lead-II acetate in 30 ml of water is then added. The mixture is heated under reflux for a further 5 minutes and then cooled to 0° C. to 5° C., and 30 ml of glacial acetic acid are added to the aqueous solution. The product thereby obtained as crystals is isolated by filtration with suction.

6.3 g (81.5% of theory) of 2-cyanoamino-4,6-dimethoxy-pyrimidine of melting point 202° C. are obtained.

The compounds of the formula (V) listed in the following Table 5 can be prepared by the process described by way of example in the preceding example:

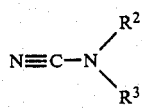 (V)

TABLE 5

| Example No. | $R^2$ | $R^3$ | Melting point (°C.) |
|---|---|---|---|
| (V-3) | H | (pyrimidine with H, CH₃) | 203 (decomp.) |
| (V-4) | H | (pyrimidine with CH₃, CH₃) | 234 |
| (V-5) | H | (pyrimidine with OCH₃, CH₃) | 258 |
| (V-6) | H | (pyrimidine with OC₂H₅, CH₃) | |
| (V-7) | H | (pyrimidine with OCH₃, Cl) | 200 |
| (V-8) | H | (pyrimidine with OC₂H₅, Cl) | |

TABLE 5-continued

| Example No. | $R^2$ | $R^3$ | Melting point (°C.) |
|---|---|---|---|
| (V-9) | H | (pyrimidine with N(CH₃)₂, Cl) | |
| (V-10) | H | (pyrimidine with SCH₃, CH₃) | |
| (V-11) | H | (pyrimidine with N(CH₃)₂, CH₃) | |
| (V-12) | H | (pyrimidine with OCHF₂, CH₃) | 174 |
| (V-13) | H | (pyrimidine with CO—CH₃, CH₃) | 174 |
| (V-14) | H | (pyrimidine with C₂H₅) | 146 |
| (V-15) | H | (pyrimidine with OH) | >300 |
| (V-16) | H | (pyrimidine with COOC₂H₅) | 126 |
| (V-17) | H | (pyrimidine) | 186 |

2-(Alkyl-cyano-amino)-pyrimidines of the formula (V) can be prepared, for example, as follows:

Example (V-18)

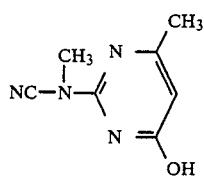

12.6 g (0.1 mole) of dimethyl sulphate are added dropwise to a solution of 15 g (0.1 mole) of 2-cyano-amino-4-hydroxy-6-methyl-pyrimidine and 4.1 g (0.1 mole) of sodium hydroxide in 60 ml of water, whereupon the reaction temperature rises from 20° C. to 40° C. After the mixture has been stirred at 20° C. for two hours, the product obtained as crystals is isolated by filtration with suction.

11.1 g (68% of theory) of 2-(methyl-cyanoamino)-4-hydroxy-6-methyl-pyrimidine of melting point 290° C. are obtained.

The following compound is obtained analogously:

Example (V-19)

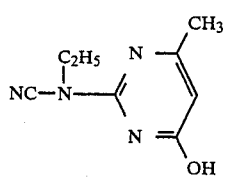

Melting point: 215° C. to 220° C.

Example (V-20)

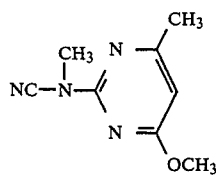

127.5 g (1 mole) of dimethyl sulphate are added dropwise to a solution of 75 g (0.5 mole) of 2-cyanoamino-4-hydroxy-6-methyl-pyrimidine—prepared according to process (b)—and 44 g (1.1 moles) of sodium hydroxide in 750 ml of water, whereupon the reaction temperature rises from 20° C. to 35° C. After the mixture has been stirred at 20° C. for twelve hours, the pH value is brought to between 9 and 10 by addition of sodium hydroxide solution and the product obtained as crystals is isolated by filtration with suction.

13 g (15% of theory) of 2-(methyl-cyanoamino)-4-methoxy-6-methyl-pyrimidine of melting point 123° C. are obtained.

The following compounds are obtained analogously:

Example (V-21)

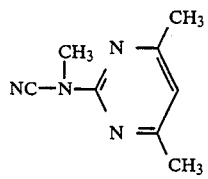

Melting point: 104° C.

Example (V-22)

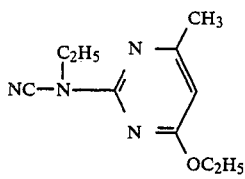

Melting point: 71° C.

PREPARATION OF FURTHER STARTING SUBSTANCES OF THE FORMULA (V)

Example (V-23)

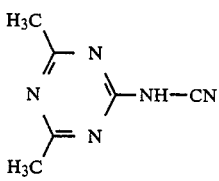

(Process (a$^1$))

A solution of 18.0 g (0.21 mole) of the disodium salt of cyanamide in 100 ml of water is added dropwise to a suspension of 28.7 g (0.2 mole) of 2-chloro-4,6-dimethyl-1,3,5-triazine in 100 ml of ice-water at a temperature of 0° C. to 5° C. in the course of 4 hours, with vigorous stirring. The mixture is then subsequently stirred at 20° C. and left to stand for 15 to 16 hours. After acidification to pH=2 with concentrated hydrochloric acid, the precipitate is filtered off with suction, washed four times with 20 ml of ice-water and dried.

19.7 g (66% of theory) of 2-cyanamino-4,6-dimethyl-1,3,5-triazine of melting point 241° C. (decomposition) are obtained.

Example (V-24)

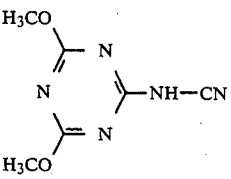

(Process (a$^2$))

A solution of 1.6 g (0.069 mole) of sodium in 20 ml of methanol is added dropwise to a suspension of 6 g (0.032 mole) of 4-chloro-2-cyanoamino-6-methoxy-1,3,5-triazine in 50 ml of methanol at 20° C. to 30° C. The mixture is then subsequently stirred at 20° C. for 15 hours. The solvent is distilled off, the residue is dissolved in 30 ml of water and the solution is acidified with hydrochloric acid. The crystals formed are filtered off with suction and dried.

5.9 g (92% of theory) of 2-cyanoamino-4,6-dimethoxy-1,3,5-triazine are obtained. The product is characterized by its $^1$H-NMR spectra.

The compounds of the formula (Va) listed in the following Table 5a can be prepared analogously to Example (V-23) and (V-24):

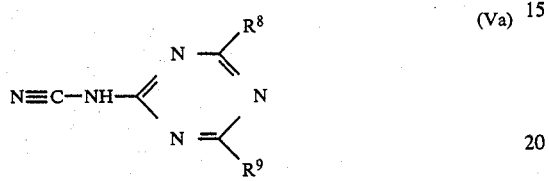
(Va)

TABLE 5a

| Example No. | $R^8$ | $R^9$ | Melting point (°C.) |
|---|---|---|---|
| V-25 | —OCH$_3$ | —N(C$_2$H$_5$)$_2$ | 114 |
| V-26 | —SCH$_3$ | —NHC$_2$H$_5$ | |
| V-27 | —OCH$_3$ | —NHCH$_3$ | 210 |
| V-28 | —Cl | —N(C$_2$H$_5$)$_2$ | 156 |
| V-29 | —OCH$_3$ | —CH$_3$ | 184 |
| V-30 | —OCH(CH$_3$)$_2$ | —CH$_3$ | |
| V-32 | —SC$_2$H$_5$ | —CH$_3$ | |
| V-33 | —SCH(CH$_3$)$_2$ | —CH$_3$ | |
| V-34 | —NHCH$_3$ | —CH$_3$ | |
| V-35 | —NHCH(CH$_3$)$_2$ | —CH$_3$ | |
| V-36 | —N(CH$_3$)$_2$ | —CH$_3$ | |
| V-37 | —OC$_2$H$_5$ | —CH$_3$ | 195 (decomposition) |
| V-38 | —C$_2$H$_5$ | —OCH$_3$ | |
| V-39 | —SCH$_3$ | —OCH$_3$ | |
| V-40 | —OC$_2$H$_5$ | —OCH$_3$ | |
| V-41 | —OCH$_3$ | —NHCH$_3$ | |
| V-42 | —OCH$_3$ | —N(CH$_3$)$_2$ | |

PREPARATION OF STARTING SUBSTANCES OF THE FORMULA (Vb)

Example (Vb-1)

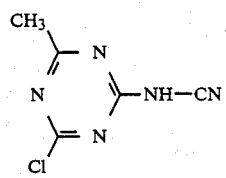

A solution of 9 g (0.043 mole) of the sodium salt of 4-chloro-2-cyanoamino-6-methoxy-1,3,5-triazine in 90 ml of water is acidified with hydrochloric acid and the crystals formed are then filtered off with suction.

6.7 g (84% of theory) of 4-chloro-2-cyanoamino-6-methoxy-1,3,5-triazine of melting point >260° C. are obtained. The product is characterized by $^1$H-NMR spectra.

The following compounds, for example, are obtained analogously:

Example (Vb-2)

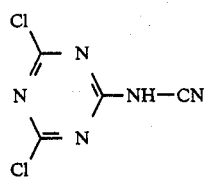

Melting point 105° C. (decomposition)

Example (Vb-3)

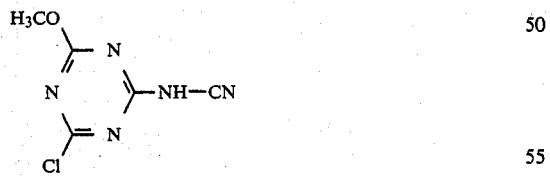

Melting point >250° C.

PREPARATION OF THE STARTING SUBSTANCES OF THE FORMULA (XI)

Example (XI-1)

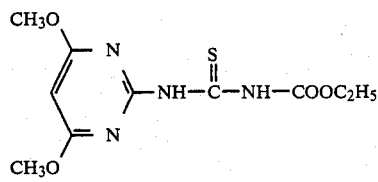

A mixture of 15.5 g (0.1 mole) of 2-amino-4,6-dimethoxy-pyrimidine, 13.1 g (0.1 mole) of ethoxycarbonyl isothiocyanate and 200 ml of acetonitrile is stirred at 60° C. for 2 hours. It is then cooled to 10° C. and the product obtained as crystals is isolated by filtration with suction.

22.5 g (79% of theory) of 1-(ethoxycarbonyl)-3-(4,6-dimethoxy-pyrimidin-2-yl)-thiourea of melting point 194° C. (decomposition) are obtained.

The compounds of the formula (XI) listed in the following Table 6 can be prepared by the process described by way of example in the preceding example:

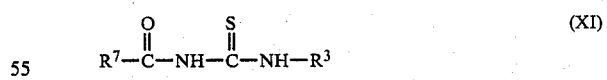
(XI)

TABLE 6

| Example No. | $R^7$ | $R^3$ | Melting point (°C.) |
|---|---|---|---|
| (XI-2) | 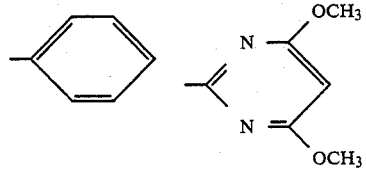 | | 189 |

TABLE 6-continued

| Example No. | R⁷ | R³ | Melting point (°C.) |
|---|---|---|---|
| (XI-3) | phenyl | 4-CH₃, 2-pyrimidinyl | 198-9 (decomp.) |
| (XI-4) | —OC₂H₅ | 4-CH₃, 6-OCH₃, 2-pyrimidinyl | 217 |
| (XI-5) | phenyl | 4-CH₃, 6-OCH₃, 2-pyrimidinyl | 190 |
| (XI-6) | —OC₂H₅ | 4,6-(CH₃)₂, 2-pyridinyl | 140 |
| (XI-7) | phenyl | 4,6-(CH₃)₂, 2-pyridinyl | 145 |
| (XI-8) | phenyl | 4-CH₃, 2-pyridinyl | 161 |
| (XI-9) | —OC₂H₅ | 4-CH₃, 2-pyridinyl | 119 |
| (XI-10) | phenyl | 4-OCHF₂, 6-CH₃, 2-pyrimidinyl | 182 |
| (XI-11) | —OC₂H₅ | 4-OCHF₂, 6-CH₃, 2-pyrimidinyl | 184-185 |
| (XI-12) | —OC₂H₅ | 4,6-(OCHF₂)₂, 2-pyrimidinyl | 173 |
| (XI-13) | —OC₂H₅ | 4-OCH₃, 6-Cl, 2-pyrimidinyl | 160-162 |
| (XI-14) | —OC₂H₅ | 4,6-Cl₂, 2-pyrimidinyl | 132-136 |
| (XI-15) | —OC₂H₅ | 4,6-(CH₃)₂, 2-pyrimidinyl | 169 |
| (XI-16) | phenyl | 4-OC₂H₅, 6-CH₃, 2-pyrimidinyl | 156 |
| (XI-17) | —OC₂H₅ | 4-OC₂H₅, 6-CH₃, 2-pyrimidinyl | — |
| (XI-18) | —OC₂H₅ | 4-OC₂H₅, 6-Cl, 2-pyrimidinyl | — |
| (XI-19) | phenyl | 4-N(CH₃)₂, 6-Cl, 2-pyrimidinyl | — |

TABLE 6-continued

| Example No. | R⁷ | R³ | Melting point (°C.) |
|---|---|---|---|
| (XI-20) | —OC$_2$H$_5$ | pyrimidine with N(CH$_3$)$_2$, Cl, CH$_3$ | 168 |
| (XI-21) | —OC$_2$H$_5$ | pyrimidine with SCH$_3$, CH$_3$ | |
| (XI-22) | phenyl | pyrimidine with SCH$_3$, CH$_3$ | |
| (XI-23) | —OC$_2$H$_5$ | pyrimidine with N(CH$_3$)$_2$, CH$_3$ | |
| (XI-24) | phenyl | pyrimidine with N(CH$_3$)$_2$, CH$_3$ | |
| (XI-25) | —OC$_2$H$_5$ | pyrimidine with OCH$_3$, OCH$_3$ | |
| (XI-26) | phenyl | pyrimidine with Cl, CH$_3$ | |
| (XI-27) | —OC$_2$H$_5$ | pyrimidine with Cl, CH$_3$ | |
| (XI-28) | phenyl | pyrimidine with CH$_3$ | 173 |
| (XI-29) | phenyl | pyrimidine with OC$_2$H$_5$, OC$_2$H$_5$ | 179 |

PREPARATION OF THE STARTING SUBSTANCES OF THE FORMULA (XII)

Example (XII-1)

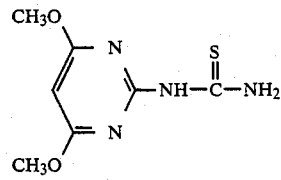

A mixture of 5.0 g (0.0175 mole) of 1-(ethoxycarbonyl)-3-(4,6-dimethoxy-pyrimidin-2-yl)-thiourea, 4.0 g (0.1 mole) of sodium hydroxide and 100 ml of water is stirred at 20° C. for 2 days. Dilute hydrochloric acid is then added dropwise, with stirring, until the solution has been rendered acid and the evolution of CO$_2$ has ended. The product obtained as crystals is isolated by filtration with suction.

3.5 g (94% of theory) of 4,6-dimethoxy-pyrimidin-2-yl-thiourea of melting point 245°–8° C. (decomposition) are obtained.

The compounds of the formula (XII) listed in the following Table 7 can be prepared by the process described by way of example in the preceding example:

TABLE 7

| Example No. | R³ | Melting point (°C.) |
|---|---|---|
| (XII-2) | pyrimidine with CH$_3$ | 264–265 (decomp.) |

TABLE 7-continued

| Example No. | R³ | Melting point (°C.) |
|---|---|---|
| (XII-3) | pyrimidine ring with CH₃ and OCH₃ | 231 (decomp.) |
| (XII-4) | pyrimidine ring with CH₃ and CH₃ | 259–260 (decomp.) |
| (XII-5) | pyrimidine ring with CH₃ | 214–215 |
| (XII-6) | pyrimidine ring with OCHF₂ and CH₃ | 192–194 |
| (XII-7) | pyrimidine ring with OCHF₂ and OCHF₂ | |
| (XII-8) | pyrimidine ring with CH₃ and CH₃ | 225–227 (decomp.) |
| (XII-9) | pyrimidine ring with OC₂H₅ and Cl | |
| (XII-10) | pyrimidine ring with N(CH₃)₂ and Cl | |
| (XII-11) | pyrimidine ring with OC₂H₅ and CH₃ | 156 |
| (XII-12) | pyrimidine ring with SCH₃ and CH₃ | |
| (XII-13) | pyrimidine ring with N(CH₃)₂ and CH₃ | |
| (XII-14) | pyrimidine ring (unsubstituted) | 263 |
| (XII-15) | pyrimidine ring with OC₂H₅ and OC₂H₅ | 166 |
| (XII-16) | pyrimidine ring with CH₃ and Cl | 248 |

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

In this test, for example, the following compounds from the preparation examples show an excellent activity: 66, 7o, 76, 79.

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, for example, the following compounds from the preparation examples show an excellent activity: 66, 70, 76, 79.

It will be appreciated that the instant specification and examples are set forth by way of illustration and not limitation, and that various modifications and changes may be made without departing from the spirit and scope of the present invention.

We claim:

1. A 1-(2-oxyaminosulphonylphenylsulphonyl)-3-triazin-yl-urea of the formula (I)

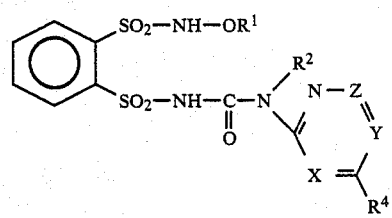

in which

R$^1$ represents C$_1$-C$_{12}$-alkyl (which is optionally substituted by fluorine, chlorine, cyano, C$_1$-C$_4$-alkoxy, C$_1$-C$_4$-alkylthio, C$_1$-C$_4$-alkylsulphinyl, C$_1$-C$_4$-alkylsulphonyl, C$_1$-C$_4$-alkyl-carbonyl, C$_1$C$_4$-alkoxy-carbonyl, C$_1$-C$_4$-alkylaminocarbonyl or di-(C$_1$-C$_4$-alkyl)-amino-carbonyl), or represents C$_3$-C$_6$-alkenyl (which is optionally substituted by fluorine, chlorine or bromine), C$_3$-C$_6$-alkinyl, C$_3$-C$_6$-cycloalkyl, C$_3$-C$_6$-cycloalkyl-C$_1$-C$_2$-alkyl or phenyl-C$_1$-C$_2$-alkyl (which is optionally substituted by fluorine, chlorine, nitro, cyano, C$_1$-C$_4$-alkyl, C$_1$-C$_4$-alkoxy or C$_1$-C$_4$-alkoxy-carbonyl), or represents benzhydryl, or represents phenyl (which is optionally substituted by fluorine, chlorine, nitro, cyano, C$_1$-C$_4$-alkyl, trifluoromethyl, C$_1$-C$_4$-alkoxy, C$_1$-C$_2$-fluoroalkoxy, C$_1$-C$_4$-alkylthio, trifluoromethylthio or C$_1$-C$_4$-alkoxycarbonyl, R$^2$ represents hydrogen or C$_1$-C$_4$-alkyl (which is optionally substituted by fluorine, chlorine, cyano, C$_1$-C$_4$-alkoxy, C$_1$-C$_4$-alkylthio, C$_1$-C$_4$-alkylsulphinyl, C$_1$-C$_4$-alkylsulphonyl, C$_1$-C$_4$-alkyl-carbonyl, C$_1$-C$_4$-alkoxy-carbonyl, C$_1$-C$_4$-alkylamino-carbonyl or di-(C$_1$-C$_4$-alkyl)-aminocarbonyl), or represents C$_3$-C$_6$-alkenyl, C$_3$-C$_6$-alkinyl or phenyl-C$_1$-C$_2$-alkyl (which is optionally substituted by fluorine, chlorine, nitro, cyano, C$_1$-C$_4$-alkyl, C$_1$-C$_4$-alkoxy or C$_1$-C$_4$-alkoxy-carbonyl), R$^4$ represents hydrogen, fluorine, chlorine, bromine, hydroxyl, C$_1$-C$_4$-alkyl (which is optionally substituted by fluorine and/or chlorine), C$_1$-C$_4$-alkoxy (which is optionally substituted by fluorine and/or chlorine), C$_1$-C$_4$-alkylthio (which is optionally substituted by fluorine and/or chlorine), amino, C$_1$-C$_4$-alkylamino or di-(C$_1$-C$_4$-alkyl)amino, X represents nitrogen, Y represents nitrogen, Z represents an optionally substituted methine bridge C-R$^6$, and R$^6$ represents hydrogen, fluorine, chlorine, bromine, hydroxyl, C$_1$-C$_4$-alkyl (which is optionally substituted by fluorine and/or chlorine), C$_1$-C$_4$-alkoxy (which is optionally substituted by fluorine and/or chlorine), C$_1$-C$_4$-alkylthio (which is optionally substituted by fluorine and/or chlorine), amino, C$_1$-C$_4$-alkylamino or di-(C$_1$-C$_4$-alkyl)-amino.

2. A compound according to claim 1, in which

R$^1$ represents C$_1$-C$_8$-alkyl (which is optionally substituted by fluorine or chlorine), C$_3$-C$_4$-alkenyl, C$_1$-C$_2$-alkoxycarbonylmethyl, phenyl, phenethyl or benzyl (which is optionally substituted by fluorine, chlorine, nitro, cyano, methyl, methoxy or methoxy-carbonyl), R$^2$ represents hydrogen, R$^4$ represents chlorine, methyl, ethyl, methoxy, difluoromethoxy or ethoxy, X represents nitrogen, Y represents nitrogen and Z represents an optionally substituted methine bridge C-R$^6$, and R$^6$ represents hydrogen, chlorine, methyl, methoxy, ethoxy, methylthio, ethylthio, methylamino or ethylamino.

3. A herbicidal composition comprising a herbicidally effective amount of a compound according to claim 1 and a diluent.

4. A method of combating unwanted vegetation which comprises applying to such vegetation or to a locus from which it is desired to exclude such vegetation a herbicidally effective amount of a compound according to claim 1 and a diluent.

* * * * *